US007803837B2

(12) United States Patent
Jung et al.

(10) Patent No.: US 7,803,837 B2
(45) Date of Patent: Sep. 28, 2010

(54) 4-OXO-4,5-DIHYDRO-FURAN-2-CARBOXYLIC ACID DERIVATIVES AND METHODS OF TREATMENT OF METABOLIC-RELATED DISORDERS THEREOF

(75) Inventors: Jae-Kyu Jung, San Diego, CA (US); Graeme Semple, San Diego, CA (US); Benjamin R. Johnson, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 11/602,551

(22) Filed: Nov. 21, 2006

(65) Prior Publication Data
US 2007/0161701 A1 Jul. 12, 2007

Related U.S. Application Data

(63) Continuation of application No. 10/578,732, filed as application No. PCT/US2004/038920 on Nov. 18, 2004.

(60) Provisional application No. 60/524,269, filed on Nov. 21, 2003.

(51) Int. Cl.
A61K 31/341 (2006.01)
A61K 31/381 (2006.01)
C07D 307/32 (2006.01)
C07D 409/04 (2006.01)

(52) U.S. Cl. .................. 514/444; 514/473; 549/60; 549/479

(58) Field of Classification Search .................. 514/444, 514/473; 549/60, 479
See application file for complete search history.

(56) References Cited

U.S. PATENT DOCUMENTS

| 4,244,958 | A | 1/1981 | Jirkovsky et al. |
| 2004/0142377 | A1 | 7/2004 | Unett et al. |
| 2006/0122240 | A1 | 6/2006 | Semple et al. |
| 2006/0167270 | A1 | 7/2006 | Semple et al. |
| 2006/0205955 | A1 | 9/2006 | Boatman et al. |
| 2006/0217562 | A1 | 9/2006 | Semple et al. |
| 2007/0032537 | A1 | 2/2007 | Semple et al. |
| 2007/0072924 | A1 | 3/2007 | Semple et al. |
| 2007/0073062 | A1 | 3/2007 | Boatman et al. |
| 2008/0139628 | A1 | 6/2008 | Behan et al. |
| 2008/0161422 | A1 | 7/2008 | Kanemitsu-Parks et al. |
| 2009/0117559 | A1 | 5/2009 | Liaw et al. |
| 2009/0258892 | A1 | 10/2009 | Boatman et al. |

FOREIGN PATENT DOCUMENTS

| WO | WO80/00025 | 1/1980 |
| WO | WO2004/032928 | 4/2004 |
| WO | WO2004/033431 | 4/2004 |
| WO | WO2004/041274 | 5/2004 |
| WO | WO2005/011677 | 2/2005 |
| WO | WO2005/044816 | 5/2005 |
| WO | WO2006/052569 | 5/2006 |
| WO | WO2006/069242 | 6/2006 |
| WO | WO2006/089009 | 8/2006 |
| WO | WO2006/127595 | 11/2006 |
| WO | WO2007/021744 | 2/2007 |

OTHER PUBLICATIONS

Gray et al., Spectroscopy Letts., (1994), vol. 27(7), pp. 935-954.*
Berge, Stephen M., et al., "Pharmaceutical salts", *Journal of Pharmaceutical Sciences*, 66(1), pp. 1-19, (1977).
Caine, Drury S. et al., "Reactions of a 3(2H)—Furanone Lithium Enolate with 4-Halocrotonates", *Synlett*, pp. 1391-1394, (1999).
Carballo-Jane et al., "Comparison of rat and dog models of vasodilation and lipolysis for the calculation of a therapeutic index for GPR109A agonists," *Journal of Pharmacological and Toxicological Methods*, Article in Press, doi:10.1016/j.vascn.2007.05.007 (2007).
Carballo-Jane et al., "Comparison of rat and dog models of vasodilation and lipolysis for the calculation of a therapeutic index for GPR109A agonists," *Journal of Pharmacological and Toxicological Methods*, 56(3). pp. 308-316, (2007).
Chang, A. Y., et al., "Ciglitazone, a New Hypoglycemic Agent. I. Studies in ob/ob and db/db Mice, Diabetic Chinese Hamsters, and Normal and Streptozotocin-Diabetic Rats", *Diabetes*, 32(9), pp. 830-838, (1983).
Coleman, Douglas L., "Diabetes-Obesity Syndromes in Mice", *Diabetes* 31(Suppl 1 Pt 2), pp. 1-6, (1982).
Coleman, D. L. et al., "Fat (fat) and Tubby (tub): Two Autosomal Recessive Mutations Causing Obesity Syndromes in the Mouse", *The Journal of Heredity*, 81(6), pp. 424-427, (1990).
Collier, T. L. et al., "Radiosynthesis and in-vivo Evaluation of the Pseudopeptide δ-Opioid Antagonist [$^{125}$I]-ITIPP(Ψ)," *J. Labelled Cpd. Radiopharm*, 42(Suppl 1):S264-266, (1999).
Cornhill, J. Fredrick, et al., "Topographic Study of Sudanophilic Lesions in Cholesterol—Fed Minipigs by Image Analysis", *Arteriosclerosis*, 5(5), pp. 415-426, (1985).
Delporte, Marie-Laure, et al. "Pre- and Post-translational negative effect of β -adrenoceptor agonists on adiponectin secretion: in vitro and in vivo studies", *Biochemical Journal*, 367(3), pp. 677-685, (2002).
Eriksson, Ulf et al., "Increased Incidence of Congenital Malformations in the Offspring of Diabetic Rats and Their Prevention by Maternal Insulin Therapy", *Diabetes*, 31(1), pp. 1-6, (1982).
Friedman, Jeffrey M. et al., "Tackling a Weighty Problem" *Cell*, 69(2), pp. 217-220, (1992).
Gennaro, A. R., et al., eds, Remington, The Science and Practice of Pharmacy, 20th Edition, Lippincott Williams & Wilkins, (2000).
Gerrity, Ross G. et al., "Diabetes-Induced Accelerated Atherosclerosis in Swine", *Diabetes*, 50(7), pp. 1654-1665, (2001).

(Continued)

*Primary Examiner*—Taofiq A Solola
(74) *Attorney, Agent, or Firm*—Fish & Richardson P.C.; Jonathan Duffield

(57) ABSTRACT

System for selecting a color shade comprising a very small number of color display cards with mixed shades of two or more colors. The system comprises means for selecting one shade among mixed shades, means for presenting the selected mixed shade as well as means for specifying the selected mixed shade for making paint in the desired color tone.

34 Claims, No Drawings

OTHER PUBLICATIONS

Gharbaoui et al., "Agonist lead identification for the high affinity niacin receptor GPR109a," *Bioorganic & Medicinal Chemistry Letters*, 17:4914-4919 (2007).

Harmon, J. G. et al., eds., Goodman and Gilman's Pharmacological Basis of Therapeutics, Chapter 36, pp. 971-1002, (2001).

Guyton, John R., "Effect of Niacin on Atherosclerotic Cardiovascular Disease", *American Journal of Cardiology*, vol. 82, pp. 18U-23U, (1998).

Higuchi, T. and V. Stella, "Pro-drugs as Novel Delivery Systems", vol. 14 of the A.C.S. • Symposium Series.

Holland, Gerald F. et al., "Heterocyclic Tetrazoles, a New Class of Lipolysis Inhibitors", *Journal of Medicinal Chemistry* 10(2), pp. 149-154, (1967).

Horikoshi, Hiroyoshi, et al. "Troglitazone (CS-045), a New Antidiabetic Drug", *Annual Report of Sankyo Research Laboratories*, vol. 46, pp. 1-57, (1994).

Hudlicky, M., Oxidation in Organic Chemistry, ACS Monograph 186 (1990).

J. Jaques, A. Collet and S. Wilen in "Enantiomers, Racemates and Resolutions", John Wiley and Sons, New York (1981).

Jirkovsky, Ivo et al., "Hypolipidemic 4,5-Dihydro-4-oxo-5,5-disubstituted-2-Furancarboxylic Acids", *J. Med Chem.*, vol. 25, pp. 1154-1156, (1982).

Jung et al., "Analogues of acifran: agonists of the high and low affinity niacin receptors, GPR109a and GPR109b," *Journal of Medicinal Chemistry*, 50:1445-1448 (2007).

Kallai-Sanfacon, M. A. et al., "Effect of AY-25,712 and Other Lipid-Lowering Agents on Liver Catalase and Liver Carnitine Acetyltransferase in Rats", *Proceedings of the Society for Experimental Biology and Medicine*, 173(3), pp. 367-371, (1983).

Koranyi, Laszlo et al., "Glucose Transporter Levels in Spontaneously Obese (db/db) Insulin-Resistant Mice", *Journal of Clinical Investigation*, 85(3), pp. 962-967, (1990).

Le Bas, M.-D. et al., "Radioiodinated Analogs of EP00652218 for the Exploration of the Tachykinin NK1 Receptor by Spect", *J. Labelled Cpd. Radiopharm*, 44(Suppl 1):S280-282, (2001).

Larock, R.C., *Comprehensive Organic Transformations, A Guide to Functional Group Preparations*, $2^{nd}$ Edition, VCH Publishers, Inc. (1999).

Lorenzen, Anna et al. "G protein-coupled receptor for nicotinic acid in mouse macrophages", *Biochemical Pharmacology*, 64(4), pp. 645-648, (2002).

Lorenzen, Anna et al., "Characterization of a G Protein-Coupled Receptor for Nicotinic Acid", *Molecular Pharmacology*, 59(2), 349-357, (2001).

Maciejewski-Lenoir et al., "Langerhans cells release prostaglandin $D_2$ in response to nicotinic acid," *Journal of Investigative Dermatology*, 126:2637-2646, (2006).

Mahboubi, Keyvan et al., "Triglyceride modulation by acifran analogs: activity towards the niacin high and low affinity G protein-coupled receptors HM74A and HM74", *Biochem. Biophys. Res. Comm.*, vol. 340, pp. 482-490, (2006).

Matsuda, Morihiro et al., "Role of Adiponectin in Preventing Vascular Stenosis. The Missing Link of Adipo-Vascular axis" *Journal of Biological Chemistry*, 277(40), pp. 37487-37491, (2002).

Meister, Herbert et al., "Reaction products from 3,5-octadiyne-2,7-diol", *Justus Liebigs Annalen der Chemie*, No. 11, pp. 1908-1914, (1974).

Remington's Pharmaceutical Sciences, 17th ed., Mack Publishing Company, Easton, Pa, p. 1418, (1985).

Richman et al., "Nicotinic acid receptor agonists differentially activate downstream effectors," *The Journal of Biological Chemistry*, 282:18028-18036, (2007).

Roche, Edward B., ed., "Bioreversible Carriers in Drug Design", *American Pharmaceutical Association and Pergamon Press*, (1987).

Royo, T. et al., "Effect of gemfibrozil on peripheral atherosclerosis and platelet activation in a pig model of hyperlipidemia", *European Journal of Clinical Investigation*, 30(10), pp. 843-852, (2000).

Semple et al., "Recent progress in the discovery of niacin receptor agonists," *Current Opinion in Drug Discovery & Development*, 10:452-459, (2007).

Semple et al., "1-Alkyl-benzotriazole-5-carboxylic acids are highly selective agonists of the human orphan G-protein-coupled receptor GPR109b," *Journal of Medicinal Chemistry*, 49:1227-1230, (2006).

Semple, "Niacin receptor agonists," *Presentation*, American Chemical Society $233^{rd}$ National Meeting & Exposition, Mar. 25, 2007-Mar. 29, 2007, Chicago, Illinois.

Semple, "Discovery of selective agonists for GPR109a and GPR109b, the high and low affinity receptors for niacin," *Presentation, GPCRs in Medicinal Chemistry*, jointly organized by the Society of Chemical Industry, Royal Society of Chemistry and the Societa Chimica Italiana, Sep. 18, 2006-Sep. 20, 2006, Verona, Italy.

Shafrir, "Diabetes in Animals," *Diabetes Mellitus*, H Rifkin and D Porte, Jr, Eds [Elsevier Science Publishing Co, New York, ed. 4, pp. 299-340, (1990)].

Skinner et al, "Fluorinated pyrazole acids are agonists of the high affinity niacin receptor GPR109a," *Poster*, $30^{th}$ National Medicinal Chemistry Symposium, Jun. 25, 2006-Jun. 29, 2006, Seattle, WA.

Smith and March, *Advanced Organic Chemistry*, $5^{th}$ Edition, Wiley-Interscience (2001).

Soga, Takatoshi et al., "Molecular identification of nicotinic acid receptor", *Biochemical and Biophysical Research Communications*, vol. 303, pp. 364-369, (2003).

Taggart et al., "(D)-β-Hydroxybutyrate inhibits adipocyte lipolysis via the nicotinic acid receptor PUMA-G," *The Journal of Biological Chemistry*, 280:26649-26652, (2005).

Truett, Gary E. et al., "Rat obesity gene fatty (*fa*) maps to chromosome 5: Evidence for homology with the mouse gene diabetes (*db*)", *Proc. Natl. Acad. Sci. USA*, 88(17), pp. 7806-7809, (1991).

Tunaru, Sorin, et al., "PUMA-G and HM74 are receptors for nicotinic acid and mediate its anti-lipolytic effect", Nature Medicine, 9(3), pp. 352-355, (2003).

Van Herk, T. et al., "Pyrazole Derivatives as Partial Agonists for the Nicotinic Acid Receptor", *Journal of Medicinal Chemistry*, 46(18), pp. 3945-3951, (2003).

Wise, Alan et al., "Molecular Identification of High and Low Affinity Receptors for Nicotinic Acid", *Journal of Biological Chemistry*, 278(11), pp. 9869-9874, (2003).

Wuts, P. G. M. et al.; *Protective Groups in Organic Synthesis*, $3^{rd}$ Edition, John Wiley and Sons, (1999).

Zhu et al., Synthesis and Mode of Action of $^{125}$I- and $^{3}$H-Labeled Thieno[2,3-c]pyridine Antagonists of Cell Adhesion Molecule Expression. *Journal of Organic Chemistry*, 67(3), 943-948, (2002)/.

Gray, Lovett, et al., "NMR Studies of Drugs. Applications of Achiral and Chiral Lanthanide Shift Reagents to Acifran Methyl Ester. LSR Binding to a Multifunctional Substrate.", *Spectroscopy Letters*, 27(7):935-954 (1994).

Guillory, J. K., "Generation of Polymorphs, Hydrates, Solvates and Amorphous Solids", pp. 183-226, in *Polymorphism in Pharmaceutical Solids*, Ed. Britain, H. G., Marcel Dekker, Inc., New York (1999).

Restriction Requirement, U.S. Appl. No. 10/578,732, mailed Sep. 26, 2007.

Non-Final Office Action, U.S. Appl. No. 10/578,732, mailed May 13, 2008.

International Search Report for PCT/US2004/038920.

International Preliminary Report on Patentability for PCT/US2004/038920.

Okamoto, "Adiponectin reduces atherosclerosis in apolipoprotein e-deficient mice", *Circulation*, 106:2767-2770 (2002).

Shen, Hong C., et al., "Novel patent publications on high-affinity nicotinic acid receptor agonists", Expert Opinion on Therapeutic Patents, (Jul. 2009), 19(7):957-967.

Martres, Paul, "HM74a agonists: Will they be the new generation of nicotinic acid?", Current Topics in Medicinal Chemistry, (2009), 9(5):428-435.

Lai, Eseng, et al., "Effects of a niacin receptor partial agonist, MK-0354, on plasma free fatty acids, lipids, and cutaneous flushing in humans", Journal of Clinical Lipidology, (Oct. 2008) 2(5):375-383.

\* cited by examiner

SEQUENCE LISTING

<160> NUMBER OF SEQ ID NOS: 2

<210> SEQ ID NO 1
<211> LENGTH: 1092
<212> TYPE: DNA
<213> ORGANISM: Homo sapien -continued

<400> SEQUENCE: 1

```
atgaatcggc accatctgca ggatcacttt ctggaaatag acaagaagaa ctgctgtgtg      60
ttccgagatg acttcattgt caaggtgttg ccgccggtgt tggggctgga gtttatcttc     120
gggcttctgg gcaatggcct tgccctgtgg attttctgtt tccacctcaa gtcctggaaa     180
tccagccgga ttttcctgtt caacctggca gtggctgact tctactgat catctgcctg      240
cccttcctga tggacaacta tgtgaggcgt tgggactgga gtttgggga catcccttgc      300
cggctgatgc tcttcatgtt ggctatgaac cgccagggca gcatcatctt cctcacggtg     360
gtggcggtag acaggtattt ccgggtggtc atccccacc acgccctgaa caagatctcc      420
aatcggacag cagccatcat ctcttgcctt ctgtggggca tcactattgg cctgacagtc     480
cacctcctga agaagaagat gccgatccag aatggcggtg caaatttgtg cagcagcttc     540
agcatctgcc ataccttcca gtggcacgaa gccatgttcc tcctggagtt cttcctgccc     600
ctgggcatca tcctgttctg ctcagccaga attatctgga gcctgcggca gagacaaatg     660
gaccggcatg ccaagatcaa gagagccatc accttcatca tggtggtggc catcgtcttt     720
gtcatctgct tccttcccag cgtggttgtg cggatccgca tcttctggct cctgcacact     780
tcgggcacgc agaattgtga agtgtaccgc tcggtggacc tggcgttctt tatcactctc     840
agcttcacct acatgaacag catgctggac cccgtggtgt actacttctc agcccatcc     900
tttcccaact tcttctccac tttgatcaac cgctgcctcc agaggaagat gacaggtgag     960
ccagataata accgcagcac gagcgtcgag ctcacagggg accccaacaa aaccagaggc    1020
gctccagagg cgttaatggc caactccggt gagccatgga gccctctta tctgggccca    1080
acctctcctt aa                                                        1092
```

<210> SEQ ID NO 2
<211> LENGTH: 363
<212> TYPE: PRT
<213> ORGANISM: Homo sapien

<400> SEQUENCE: 2

```
Met Asn Arg His His Leu Gln Asp His Phe Leu Glu Ile Asp Lys Lys
1               5                   10                  15

Asn Cys Cys Val Phe Arg Asp Asp Phe Ile Val Lys Val Leu Pro Pro
            20                  25                  30

Val Leu Gly Leu Glu Phe Ile Phe Gly Leu Leu Gly Asn Gly Leu Ala
        35                  40                  45

Leu Trp Ile Phe Cys Phe His Leu Lys Ser Trp Lys Ser Ser Arg Ile
    50                  55                  60

Phe Leu Phe Asn Leu Ala Val Ala Asp Phe Leu Ile Ile Cys Leu
65                  70                  75                  80

Pro Phe Leu Met Asp Asn Tyr Val Arg Arg Trp Asp Trp Lys Phe Gly
                85                  90                  95

Asp Ile Pro Cys Arg Leu Met Leu Phe Met Leu Ala Met Asn Arg Gln
            100                 105                 110

Gly Ser Ile Ile Phe Leu Thr Val Val Ala Val Asp Arg Tyr Phe Arg
        115                 120                 125

Val Val His Pro His His Ala Leu Asn Lys Ile Ser Asn Arg Thr Ala
    130                 135                 140

Ala Ile Ile Ser Cys Leu Leu Trp Gly Ile Thr Ile Gly Leu Thr Val
145                 150                 155                 160
```

```
His Leu Leu Lys Lys Lys Met Pro Ile Gln Asn Gly Gly Ala Asn Leu
            165             170                 175
Cys Ser Ser Phe Ser Ile Cys His Thr Phe Gln Trp His Glu Ala Met
            180             185                 190
Phe Leu Leu Glu Phe Phe Leu Pro Leu Gly Ile Ile Leu Phe Cys Ser
            195             200                 205
Ala Arg Ile Ile Trp Ser Leu Arg Gln Arg Gln Met Asp Arg His Ala
    210             215             220
Lys Ile Lys Arg Ala Ile Thr Phe Ile Met Val Val Ala Ile Val Phe
225             230             235                 240
Val Ile Cys Phe Leu Pro Ser Val Val Val Arg Ile Arg Ile Phe Trp
                245             250                 255
Leu Leu His Thr Ser Gly Thr Gln Asn Cys Glu Val Tyr Arg Ser Val
                260             265             270
Asp Leu Ala Phe Phe Ile Thr Leu Ser Phe Thr Tyr Met Asn Ser Met
        275             280             285
Leu Asp Pro Val Val Tyr Tyr Phe Ser Ser Pro Ser Phe Pro Asn Phe
    290             295             300
Phe Ser Thr Leu Ile Asn Arg Cys Leu Gln Arg Lys Met Thr Gly Glu
305             310             315                 320
Pro Asp Asn Asn Arg Ser Thr Ser Val Glu Leu Thr Gly Asp Pro Asn
                325             330                 335
Lys Thr Arg Gly Ala Pro Glu Ala Leu Met Ala Asn Ser Gly Glu Pro
            340             345             350
Trp Ser Pro Ser Tyr Leu Gly Pro Thr Ser Pro
            355             360
```

4-OXO-4,5-DIHYDRO-FURAN-2-CARBOXYLIC ACID DERIVATIVES AND METHODS OF TREATMENT OF METABOLIC-RELATED DISORDERS THEREOF

CROSS-REFERENCE TO RELATED APPLICATIONS

This application is a continuation of U.S. Ser. No. 10/578,732, filed Nov. 22, 2006 which is a national phase application under 35 U.S.C. §371 of PCT International Application No. PCT/US2004/038920, filed Nov. 18, 2004, which claims the benefit of U.S. Provisional Patent Application, Ser. No. 60/524,269, filed Nov. 21, 2003, the disclosure of which is herein incorporated by reference in its entirety.

FIELD OF THE INVENTION

The present invention relates to certain 4-oxo-4,5-dihydro-furan-2-carboxylic acid and ester derivatives and pharmaceutically acceptable salts thereof, which exhibit useful pharmacological properties, for example as agonists for the nicotinic acid receptor, RUP25. Also provided by the present invention are pharmaceutical compositions containing one or more compounds of the invention and methods of using the compounds and compositions of the invention in the treatment of metabolic-related disorders, including dyslipidemia, atherosclerosis, coronary heart disease, insulin resistance, type 2 diabetes, Syndrome-X, and the like. In addition, the present invention also provides for the use of the compounds of the invention in combination with other active agents such as those belonging to the class of α-glucosidase inhibitors, aldose reductase inhibitors, biguanides, HMG-CoA reductase inhibitors, squalene synthesis inhibitors, fibrates, LDL catabolism enhancers, angiotensin converting enzyme (ACE) inhibitors, insulin secretion enhancers, thiazolidinedione, and the like.

BACKGROUND OF THE INVENTION

Compounds of the Invention as Antilipolytic Agents

Atherosclerosis and stroke are the numbers one and number three leading causes of death of both men and women in the United States. Type 2 diabetes is a public health problem that is serious, widespread and increasing. Elevated levels of low density lipoprotein (LDL) cholesterol or low levels of high density lipoprotein (HDL) cholesterol are, independently, risk factors for atherosclerosis and associated cardiovascular pathologies. In addition, high levels of plasma free fatty acids are associated with insulin resistance and type 2 diabetes. One strategy for decreasing LDL-cholesterol, increasing HDL-cholesterol and decreasing plasma free fatty acids is to inhibit lipolysis in adipose tissue. This approach involves regulation of hormone sensitive lipase, which is the rate-limiting enzyme in lipolysis. Lipolytic agents increase cellular levels of cAMP, which leads to activation of hormone sensitive lipase within adipocytes. Agents that lower intracellular cAMP levels, by contrast, would be antilipolytic.

It is also worth noting in passing that an increase in cellular levels of cAMP down-regulates the secretion of adiponectin from adipocytes [Delporte, M L et al. *Biochem J* (2002) July]. Reduced levels of plasma adiponectin have been associated with metabolic-related disorders, including atherosclerosis, coronary heart disease, insulin resistance and type 2 diabetes [Matsuda, M et al. *J Biol Chem* (2002) July and reviewed therein].

Nicotinic acid (niacin, pyridine-3-carboxylic acid) is a water-soluble vitamin required by the human body for health, growth and reproduction; a part of the Vitamin B complex. Nicotinic acid is also one of the oldest used drugs for the treatment of dyslipidemia. It is a valuable drug in that it favorably affects virtually all of the lipid parameters listed above [Goodman and Gilman's Pharmacological Basis of Therapeutics, editors Harmon J G and Limbird L E, Chapter 36, Mahley R W and Bersot T P (2001) pages 971-1002]. The benefits of nicotinic acid in the treatment or prevention of atherosclerotic cardiovascular disease have been documented in six major clinical trials [Guyton J R (1998) Am J Cardiol 82:18U-23U]. Nicotinic acid and related derivatives, such as, acipimox have recently been discussed [Lorenzen, A et al (2001) Molecular Pharmacology 59:349-357].

Nicotinic acid inhibits the production and release of free fatty acids from adipose tissue, likely via an inhibition of adenylyl cyclase, a decrease in intracellular cAMP levels and a concomitant decrease in hormone sensitive lipase activity. Agonists that down-regulate hormone sensitive lipase activity leading to a decrease in plasma free fatty acid levels are likely to have therapeutic value. The consequence of decreasing plasma free fatty acids is two-fold. First, it will ultimately lower LDL-cholesterol and raise HDL-cholesterol levels, independent risk factors, thereby reducing the risk of mortality due to cardiovascular incidence subsequent to atheroma formation. Second, it will provide an increase in insulin sensitivity in individuals with insulin resistance or type 2 diabetes. Unfortunately, the use of nicotinic acid as a therapeutic is partially limited by a number of associated, adverse side-effects. These include flushing, free fatty acid rebound and liver toxicity.

The rational development of novel, nicotinic acid receptor agonists that have fewer side-effects will be valuable, but to date this has been hindered by the inability to molecularly identify the nicotinic acid receptor. Furthermore, other receptors of the same class may exist on the surface of adipocytes and similarly decrease hormone sensitive lipase activity through a reduction in the level of intracellular cAMP but without the elicitation of adverse effects such as flushing, thereby representing promising novel therapeutic targets. Recent work suggests that nicotinic acid probably acts through a specific GPCR [Lorenzen A, et al. (2001) Molecular Pharmacology 59:349-357 and reviewed therein]. Further work has suggested that the effects of nicotinic acid on macrophages, spleen and probably adipocytes are mediated via this specific GPCR [Lorenzen A, et al. (2002) Biochemical Pharmacology 64:645-648 and reviewed therein].

SUMMARY OF THE INVENTION

One aspect of the present invention encompasses 4-oxo-4,5-dihydro-furan-2-carboxylic acid and ester derivatives as shown in Formula (I):

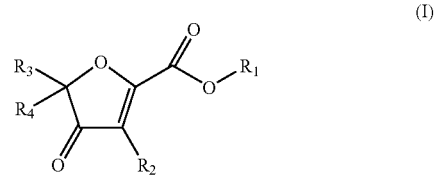

wherein:

$R_1$ is H or $C_{1-6}$ alkyl;

$R_2$ is H, halogen, $C_{1-4}$ alkyl or $C_{1-4}$ haloalkyl;

$R_3$ is aryl, $C_{3-7}$ cycloalkyl, $C_{3-7}$ cycloalkenyl, heteroaryl, $C_{3-7}$ heterocycloalkyl or $C_{3-7}$ heterocycloalkenyl wherein each are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol; and $R_4$ is selected from the group consisting of H, $C_{1-6}$ alkyl, $C_{3-6}$-cycloalkoxy and $C_{1-6}$ haloalkyl wherein each are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, nitro and thiol; or a pharmaceutically acceptable salt, hydrate or solvate thereof.

In some embodiments, when $R_1$ and $R_2$ are both H and $R_4$ is methyl, then $R_3$ is not phenyl or 4-chlorophenyl.

In some embodiments, when $R_1$ and $R_2$ are both H and $R_4$ is isopropyl, then $R_3$ is not phenyl.

In some embodiments, when $R_1$ and $R_4$ are both methyl and $R_2$ is H, then $R_3$ is not phenyl.

One aspect of the present invention encompasses 4-oxo-4,5-dihydro-furan-2-carboxylic acid and ester derivatives as shown in Formula (I):

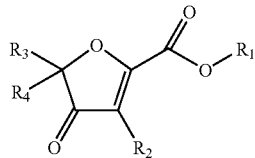

(I)

or a pharmaceutically acceptable salt, hydrate or solvate thereof, wherein:

$R_1$ is H or $C_{1-6}$ alkyl;

$R_2$ is H, halogen, $C_{1-4}$ alkyl or $C_{1-4}$ haloalkyl; and

A) $R_3$ is aryl, $C_{3-7}$ cycloalkyl, $C_{3-7}$ cycloalkenyl, heteroaryl, $C_{3-7}$ heterocycloalkyl or $C_{3-7}$ heterocycloalkenyl wherein each are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol; and $R_4$ is selected from the group consisting of H, ethyl, n-propyl, $C_{4-6}$ alkyl, $C_{3-6}$-cycloalkyl and $C_{1-6}$ haloalkyl wherein each are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, nitro and thiol; or B) $R_3$ is a substituted phenyl, 2-chlorophenyl, 3-chlorophenyl, naphthyl, $C_{3-7}$ cycloalkyl, $C_{3-7}$ cycloalkenyl, heteroaryl, $C_{3-7}$ heterocycloalkyl or $C_{3-7}$ heterocycloalkenyl wherein the 2-chlorophenyl, 3-chlorophenyl, naphthyl, $C_{3-7}$ cycloalkyl, $C_{3-7}$ cycloalkenyl, heteroaryl, $C_{3-7}$ heterocycloalkyl and $C_{3-7}$ heterocycloalkenyl are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol; and $R_4$ is selected from the group consisting of H, $C_{1-6}$ alkyl, $C_{3-6}$-cycloalkyl and $C_{1-6}$ haloalkyl wherein each are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, nitro and thiol.

In some embodiments, $R_4$ is selected from the group consisting of H, ethyl, n-propyl, $C_{4-6}$ alkyl and $C_{1-6}$ haloalkyl wherein each are optionally substituted with 1 to 5 substituents selected from the group consisting of $C_{1-6}$ acyloxy, $C_{2-6}$ alkenyl, $C_{1-6}$ alkoxy, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, nitro and thiol.

In some embodiments, $R_4$ is $C_{3-6}$-cycloalkyl optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, nitro and thiol.

One aspect of the present invention encompasses pharmaceutical compositions comprising at least one compound according to Formula (I), as described herein, in combination with a pharmaceutically acceptable carrier.

In some embodiments, the pharmaceutical composition further comprises one or more agents selected from the group consisting of α-glucosidase inhibitor, aldose reductase inhibitor, biguanide, HMG-CoA reductase inhibitor, squalene synthesis inhibitor, fibrate, LDL catabolism enhancer, angiotensin converting enzyme inhibitor, insulin secretion enhancer and thiazolidinedione.

One aspect of the present invention pertains to methods of treatment of a metabolic-related disorder comprising administering to an individual in need of such treatment a therapeutically-effective amount of a compound according to Formula (I), as described herein or a pharmaceutical composition thereof.

One aspect of the present invention pertains to methods of modulating a RUP25 receptor comprising contacting the receptor with a compound according to Formula (I), as described herein or a pharmaceutical composition thereof.

One aspect of the present invention pertains to methods of modulating a RUP25 receptor for the treatment of a metabolic-related disorder in an individual in need of such modulation comprising contacting the receptor with a therapeutically-effective amount of a compound according to Formula (I), as described herein or a pharmaceutical composition thereof.

One aspect of the present invention pertains to methods of raising HDL in an individual comprising administering to the individual a therapeutically-effective amount of a compound according to Formula (I), as described herein or a pharmaceutical composition thereof.

One aspect of the present invention pertains to a compound of Formula (I), as described herein, for use in a method of treatment of the human or animal body by therapy.

One aspect of the present invention pertains to a compound of Formula (I), as described herein, for use in a method of treatment of a metabolic-related disorder of the human or animal body by therapy.

One aspect of the present invention pertains to the use of compounds of Formula (I), as described herein, in a method of raising HDL of the human or animal body by therapy.

One aspect of the present invention pertains to the use of compounds of Formula (I), as described herein, for the manufacture of a medicament for use in the treatment of a metabolic-related disorder.

One aspect of the present invention pertains to the use of compounds of Formula (I), as described herein, for the manufacture of a medicament for use in raising HDL in an individual.

In some embodiments of the present invention, the metabolic-related disorder is of the group consisting of dyslipidemia, atherosclerosis, coronary heart disease, insulin resistance, obesity, impaired glucose tolerance, atheromatous disease, hypertension, stroke, Syndrome X, heart disease and type 2 diabetes. In some embodiments the metabolic-related disorder is dyslipidemia, atherosclerosis, coronary heart disease, insulin resistance and type 2 diabetes. In some embodiments the metabolic-related disorder is dyslipidemia. In some embodiments the metabolic-related disorder is atherosclerosis. In some embodiments the metabolic-related disorder is coronary heart disease. In some embodiments the metabolic-related disorder is insulin resistance. In some embodiments the metabolic-related disorder is type 2 diabetes.

One aspect of the present invention encompasses a method of producing a pharmaceutical composition comprising admixing at least one compound according to Formula (I), as described herein and a pharmaceutically acceptable carrier or excipient.

These and other aspects of the invention disclosed herein will be set forth in greater detail as the patent disclosure proceeds.

DETAILED DESCRIPTION OF THE INVENTION

The scientific literature has adopted a number of terms, for consistency and clarity, the following definitions will be used throughout this patent document.

The term "ADMINISTERING" as used herein refers to a step for introducing a compound of the present invention into an individual. The term "administering" shall further encompass the prevention, inhibition or amelioration of the various conditions described herein with a compound of the invention or with a compound which may not be specifically disclosed, but which converts to a specified compound of the invention in vivo after administration to the individual. Various routes can be used for administering a compound, these include, but not limited to oral, parenteral, dermal, injection, aerosol, and the like; additional routes of administration are described herein.

AGONISTS shall mean moieties that interact and activate the receptor, such as the RUP25 receptor and initiates a physiological or pharmacological response characteristic of that receptor. For example, when moieties activate the intracellular response upon binding to the receptor or enhance GTP binding to membranes.

TABLE 1

| AMINO ACID ABBREVIATIONS used herein are set out in TABLE 1: | | |
|---|---|---|
| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

The term ANTAGONISTS is intended to mean moieties that competitively bind to the receptor at the same site as agonists (for example, the endogenous ligand), but which do not activate the intracellular response initiated by the active form of the receptor and can thereby inhibit the intracellular responses by agonists or partial agonists. Antagonists do not diminish the baseline intracellular response in the absence of an agonist or partial agonist.

ATHEROSCLEROSIS is intended herein to encompass disorders of large and medium-sized arteries that result in the progressive accumulation within the intima of smooth muscle cells and lipids.

Chemical Group, Moiety or Radical:

The term "$C_{1-6}$ acyl" denotes a $C_{1-6}$ alkyl radical attached to a carbonyl wherein the definition of alkyl has the same definition as described herein; some examples include but not limited to, acetyl, propionyl, n-butanoyl, iso-butanoyl, sec-butanoyl, t-butanoyl (i.e., pivaloyl), pentanoyl, and the like.

The term "$C_{1-6}$ acyloxy" denotes an acyl radical attached to an oxygen atom wherein acyl has the same definition has described herein; some examples include but not limited to acetyloxy, propionyloxy, butanoyloxy, iso-butanoyloxy, sec-butanoyloxy, t-butanoyloxy, and the like.

The term "$C_{2-6}$ alkenyl" denotes a radical containing 2 to 6 carbons wherein at least one carbon-carbon double bond is present, some embodiments are 2 to 3 carbons and some embodiments have 2 carbons. Both E and Z isomers are embraced by the term "alkenyl." Furthermore, the term "alkenyl" includes dienes. Accordingly, if more than one double bond is present, then the bonds may be all E or Z or a mixtures of E and Z. Examples of an alkenyl include vinyl, propenyl, alkyl, isopropenyl, 2-methyl-propenyl1-methyl-propenyl, but-1-enyl, but-2-enyl, but-3-enyl, buta-1,3-dienyl, and the like.

The term "$C_{1-6}$ alkoxy" denotes an alkyl radical, as defined herein, attached directly to an oxygen atom. Examples include methoxy, ethoxy, n-propoxy, iso-propoxy, n-butoxy, t-butoxy, iso-butoxy, sec-butoxy, and the like.

The term "$C_{1-6}$ alkyl" denotes a straight or branched carbon radical containing the number of carbons as indicated, for examples, in some embodiments, alkyl is a "$C_{1-4}$ alkyl" and the group contains 1 to 4 carbons, in still other embodiments, alkyl is a "$C_{2-6}$ alkyl" and the group contains 2 to 6 carbons. In some embodiments alkyl contains 1 to 3 carbons, some embodiments contain 1 to 2 carbons and some embodiments contain 1 carbon. Examples of an alkyl include, but not limited to, methyl, ethyl, n-propyl, iso-propyl, n-butyl, iso-butyl, t-butyl, sec-butyl, and the like.

The term "$C_{1-6}$ alkylsulfinyl" denotes a $C_{1-6}$ alkyl radical attached to a sulfoxide radical of the formula: —S(O)— wherein the alkyl radical has the same definition as described herein. Examples include, but not limited to, methylsulfinyl, ethylsulfinyl, n-propylsulfinyl, iso-propylsulfinyl, n-butylsulfinyl, sec-butylsulfinyl, iso-butylsulfinyl, t-butyl, and the like.

The term "$C_{1-6}$ alkylsulfonyl" denotes a $C_{1-6}$ alkyl radical attached to a sulfone radical of the formula: —S(O)$_2$— wherein the alkyl radical has the same definition as described herein. Examples include, but not limited to, methylsulfonyl, ethylsulfonyl, n-propylsulfonyl, iso-propylsulfonyl, n-butylsulfonyl, sec-butylsulfonyl, iso-butylsulfonyl, t-butylsulfonyl, and the like.

The term "$C_{1-6}$ alkylthio" denotes a $C_{1-6}$ alkyl radical attached to a sulfide group of the formula: —S— wherein the alkyl radical has the same definition as described herein. Examples include, but not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butyl, and the like.

The term "$C_{2-6}$ alkynyl" denotes a radical containing 2 to 6 carbons and at least one carbon-carbon triple bond, some embodiments are 2 to 4 carbons and some embodiments have 2 carbons. Examples of an alkynyl include, but not limited to, ethynyl, prop-1-ynyl, 3-prop-2-ynyl, but-1-ynyl, 1-methyl-prop-2-ynyl, buta-1,3-diynyl, and the like. The term "alkynyl" includes dynes.

The term "amino" denotes the group —NH$_2$.

The term "$C_{1-6}$ alkylamino" denotes one alkyl radical attached to an amino radical wherein the alkyl radical has the same meaning as described herein. Some examples include, but not limited to, methylamino, ethylamino, n-propylamino, iso-propylamino, n-butylamino, sec-butylamino, iso-butylamino, t-butylamino, and the like. Some embodiments are "$C_{1-2}$ alkylamino."

The term "aryl" denotes an aromatic ring radical containing 6 to 10 ring carbons. Examples include phenyl and naphthyl.

The term "carbo-$C_{1-6}$-alkoxy" denotes a $C_{1-6}$ alkyl ester of a carboxylic acid, wherein the alkyl group is as defined herein. Examples include, but not limited to, carbomethoxy, carboethoxy, carbopropoxy, carboisopropoxy, carbobutoxy, carbo-sec-butoxy, carbo-iso-butoxy, carbo-t-butoxy, and the like.

The term "carboxamide" refers to the group —CONH$_2$.

The term "carboxy" or "carboxyl" denotes the group —CO$_2$H; also referred to as a carboxylic acid group.

The term "cyano" denotes the group —CN.

The term "$C_{3-7}$ cycloalkyl" denotes a saturated ring radical containing 3 to 7 carbons; some embodiments, contain 3 to 6 carbons, some embodiments contain 3 to 5 carbons; some embodiments contain 3 to 4 carbons. Examples include, cyclopropyl, cyclobutyl, cyclopentyl, cyclohexyl.

The term "$C_{3-7}$ cycloalkenyl" denotes a $C_{3-7}$ cycloalkyl, as defined herein, wherein there is at least one endocyclic double bond present, some embodiments, contain 3 to 6 carbons, some embodiments contain 3 to 5 carbons; some embodiments contain 3 to 4 carbons. Examples include, cyclopropyl, cyclobutyl, cyclopentyl, cyclohexyl.

The term "$C_{2-6}$ dialkylamino" denotes an amino substituted with two of the same or different alkyl radicals wherein alkyl radical has the same definition as described herein. A $C_{2-6}$ dialkylamino may be represented by the following groups:

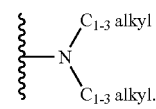

Examples of $C_{2-6}$ dialkylamino include, but not limited to, dimethylamino, methylethylamino, diethylamino, methylpropylamino, methylisopropylamino, and the like.

The term "$C_{1-6}$ haloalkoxy" denotes a haloalkyl, as defined herein, which is directly attached to an oxygen atom. Examples include, but not limited to, difluoromethoxy, trifluoromethoxy, 2,2,2-trifluoroethoxy, pentafluoroethoxy, and the like.

The term "$C_{1-6}$ haloalkyl" denotes an alkyl group wherein the alkyl is substituted with halogen ranging from one to fully substituted, wherein a fully substituted haloalkyl can be represented by the formula $C_hL_{2h+1}$ wherein L is a halogen and "h" represents the number of carbon atoms; when more than one halogen is present then the halogens may be the same or different and selected from the group consisting of F, Cl, Br and I; it is understood that the terms "alkyl" and "halogen" have the same definition as found herein. In some embodiments, haloalkyl is a "$C_{1-4}$ haloalkyl" and the group contains 1 to 4 carbons, some embodiments contain 1 to 3 carbons, some embodiments contain 1 to 2 carbons, some embodiments contain 1 carbon. When the haloalkyl is fully substituted with halogen atoms, this group is referred herein as a perhaloalkyl, one example, is an alkyl fully substituted with fluorine atoms and is referred to herein as a "perfluoroalkyl." In some embodiments, examples of a haloalkyl include, but not limited to, difluoromethyl, fluoromethyl, 2,2,2-trifluoro-ethyl, 2,2-difluoro-ethyl, 2-fluoro-ethyl, 1,2,2-trifluoro-ethyl, 1,2-difluoro-ethyl, 1,1-difluoro-ethyl, 1,1,2-trifluoro-ethyl, 3,3,3-trifluoro-propyl, 2,2-difluoro-propyl, 3,3-difluoro-propyl, 3-fluoro-propyl, 2,3,3-trifluoro-propyl, 2,3-Difluoro-propyl, 2,2,3,3,3-pentafluoro-propyl, 2,2,3,3-tetrafluoro-propyl, 2,2,3-trifluoro-propyl, 1,2,3,3-tetrafluoro-propyl, 1,2,3-trifluoro-propyl, 3,3-difluoro-propyl, 1,2,2,3-tetrafluoro-propyl, 4,4-difluoro-butyl, 3,3-difluoro-butyl, 4,4,4-trifluoro-butyl, 3,3-difluoro-butyl, and the like. In some embodiments, examples of a perfluoroalkyl include, but not limited to, trifluoromethyl, pentafluoroethyl, heptafluoropropyl, 1,2,2,2-tetrafluoro-1-trifluoromethyl-ethyl, and the like.

The term "$C_{1-6}$ haloalkylsulfinyl" denotes a haloalkyl radical attached to a sulfoxide group of the formula: —S(O)— wherein the haloalkyl radical has the same definition as described herein.

The term "$C_{1-6}$ haloalkylsulfonyl" denotes a haloalkyl radical attached to a sulfone group of the formula: —S(O)$_2$— wherein haloalkyl has the same definition as described herein.

The term "$C_{1-6}$ haloalkylthio" denotes a haloalkyl radical directly attached to a sulfur atom wherein the haloalkyl has the same meaning as described herein.

The term "halogen" or "halo" denotes to a fluoro, chloro, bromo or iodo group.

The term "$C_{3-7}$ heterocycloalkyl" denotes a cycloalkyl, as defined herein, wherein one, two or three ring carbons are replaced with a heteroatom, such as, O, S, N, wherein the N is substituted with H, $C_{1-4}$ acyl or $C_{1-4}$ alkyl and ring carbon atoms optionally substituted with oxo or a thiooxo thus forming a carbonyl or thiocarbonyl group. The heterocyclic group is a 3-, 4-, 5-, 6- or 7-membered containing ring. Examples of a heterocyclic group include but not limited to aziridin-1-yl, aziridin-2-yl, azetidin-1-yl, azetidin-2-yl, azetidin-3-yl, piperidin-1-yl, piperidin-4-yl, morpholin-4-yl, piperzin-1-yl, piperzin-4-yl, pyrrolidin-1-yl, pyrrolidin-3-yl, and the like.

The term "$C_{3-7}$ heterocycloalkenyl" denotes a cycloalkenyl, as defined herein, wherein one, two or three ring carbons are replaced with a heteroatom, such as, O, S, N, wherein the N is substituted with H, $C_{1-4}$ acyl or $C_{1-4}$ alkyl and ring carbon atoms optionally substituted with oxo or a thiooxo thus forming a carbonyl or thiocarbonyl group. The heterocyclic group is a 3-, 4-, 5-, 6- or 7-membered containing ring. Examples of a heterocyclic group include but not limited to aziridin-1-yl, aziridin-2-yl, azetidin-1-yl, azetidin-2-yl, azetidin-3-yl, piperidin-1-yl, piperidin-4-yl, morpholin-4-yl, piperzin-1-yl, piperzin-4-yl, pyrrolidin-1-yl, pyrrolidin-3-yl, and the like.

The term "heteroaryl" denotes an aromatic ring system that may be a single ring or two fused rings containing 2 to 9 carbons and at least one ring heteroatom selected from O, S and N. Examples of heteroaryl groups include, but not limited to, 5-membered heteroaryl including isoxazolyl, isothiazolyl, pyrazolyl, pyrrolyl, furanyl, thienyl, oxazolyl, thiazolyl, imidazolyl, oxadiazolyl, thiadiazolyl, triazolyl, oxadiazolyl, thiadiazolyl, and the like; 6-membered heteroaryl including, pyridyl, pyrazinyl, pyridazinyl, pyrimidinyl, triazinyl, and the like; and two fused ring heteroaryl including benzofuranyl, quinolinyl, isoquinolinyl, benzoxazolyl, benzothiazolyl, benzimidazolyl, quinazolinyl, quinoxalinyl, and the like.

The term "hydroxyl" denotes the group —OH.

The term "nitro" denotes the group —NO$_2$.

The term "thiol" denotes the group —SH.

The term CODON shall mean a grouping of three nucleotides (or equivalents to nucleotides) which generally comprise a nucleoside (adenosine (A), guanosine (G), cytidine (C), uridine (U) and thymidine (T)) coupled to a phosphate group and which, when translated, encodes an amino acid.

The term COMPOSITION shall mean a material comprising at least two compounds or two components; for example and without limitation, a Pharmaceutical Composition is a Composition comprising a compound of the present invention and a pharmaceutically acceptable carrier.

The term COMPOUND EFFICACY shall mean a measurement of the ability of a compound to inhibit or stimulate receptor functionality, as opposed to receptor binding affinity.

The term CONSTITUTIVELY ACTIVATED RECEPTOR shall mean a receptor subject to constitutive receptor activation.

The term CONSTITUTIVE RECEPTOR ACTIVATION shall mean stabilization of a receptor in the active state by means other than binding of the receptor with its endogenous ligand or a chemical equivalent thereof.

The terms CONTACT or CONTACTING shall mean bringing the indicated moieties together, whether in an in vitro system or an in vivo system. Thus, "contacting" a RUP25 receptor with a compound of the invention includes the administration of a compound of the present invention to an individual, for example a human, having a RUP25 receptor, as well as, for example, introducing a compound of the invention into a sample containing a cellular or more purified preparation containing a RUP25 receptor.

CORONARY HEART DISEASE is intended herein to encompass disorders comprising a narrowing of the small blood vessels that supply blood and oxygen to the heart. Coronary heart disease usually results from the build up of fatty material and plaque. As the coronary arteries narrow, the flow of blood to the heart can slow or stop. Coronary heart disease can cause chest pain (stable angina), shortness of breath, heart attack or other symptoms.

DECREASE is used to refer to a reduction in a measurable quantity and is used synonymously with the terms "reduce", "diminish", "lower" and "lessen".

DIABETES as used herein is intended to encompass the usual diagnosis of DIABETES made from any of the methods including, but not limited to, the following list: symptoms of diabetes (e.g. polyuria, polydipsia, polyphagia) plus casual plasma glucose levels of greater than or equal to 200 mg/dl, wherein casual plasma glucose is defined any time of the day regardless of the timing of meal or drink consumption; 8 hour fasting plasma glucose levels of less than or equal to 126 mg/dl; and plasma glucose levels of greater than or equal to 200 mg/dl 2 hours following oral administration of 75 g anhydrous glucose dissolved in water.

The phrase DISORDERS OF LIPID METABOLISM is intended herein to include, but not be limited to, dyslipidemia.

The term DYSLIPIDEMIA is intended herein to encompass disorders comprising any one of elevated level of plasma free fatty acids, elevated level of plasma cholesterol, elevated level of LDL-cholesterol, reduced level of HDL-cholesterol and elevated level of plasma triglycerides.

The phrase IN NEED OF TREATMENT, as used herein, refers to a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, that includes the knowledge that the individual is ill or will be ill, as the result of a disease, condition or disorder that is treatable by the compounds of the invention. Further, the phrase "in need of treatment" also refers to the "prophylaxis" of an individual which is the judgment made by the caregiver that the individual will become ill. In this context, the compounds of the invention are used in a protective or preventive manner. Accordingly, "in need of treatment" refers to the judgment of the caregiver that the individual is already ill or will become ill and the compounds of the present invention can be used to alleviate, inhibit, ameliorate or prevent the disease, condition or disorder.

The term INDIVIDUAL as used herein refers to any animal, including mammals, for example, mice, rats, other rodents, rabbits, dogs, cats, swine, cattle, sheep, horses or primates and in one embodiment, humans.

The terms INHIBIT or INHIBITING, in relationship to the term "response" shall mean that a response is decreased or prevented in the presence of a compound as opposed to in the absence of the compound.

INSULIN RESISTANCE as used herein is intended to encompass the usual diagnosis of insulin resistance made by any of a number of methods, including but not restricted to: the intravenous glucose tolerance test or measurement of the fasting insulin level. It is well known that there is an excellent correlation between the height of the fasting insulin level and the degree of insulin resistance. Therefore, one could use elevated fasting insulin levels as a surrogate marker for insulin resistance for the purpose of identifying which normal glucose tolerance (NGT) individuals have insulin resistance. A diagnosis of insulin resistance can also be made using the euglycemic glucose clamp test.

The term INVERSE AGONISTS shall mean moieties that bind the endogenous form of the receptor or to the constitutively activated form of the receptor and which inhibit the baseline intracellular response initiated by the active form of the receptor below the normal base level of activity which is observed in the absence of agonists or partial agonists or decrease GTP binding to membranes. In some embodiments, the baseline intracellular response is inhibited in the presence of the inverse agonist by at least 30%, in other embodiments, by at least 50% and in still other embodiments, by at least 75%, as compared with the baseline response in the absence of the inverse agonist.

The term LIGAND shall mean an endogenous, naturally occurring molecule specific for an endogenous, naturally occurring receptor.

The phrase METABOLIC-RELATED DISORDERS is intended herein to include, but not be limited to, dyslipidemia, atherosclerosis, coronary heart disease, insulin resistance, obesity, impaired glucose tolerance, atheromatous disease, hypertension, stroke, Syndrome X, heart disease and type 2 diabetes.

As used herein, the terms MODULATE or MODULATING shall mean to refer to an increase or decrease in the amount, quality, response or effect of a particular activity, function or molecule.

The term PHARMACEUTICAL COMPOSITION shall mean a composition for preventing, treating or controlling a disease state or condition comprising at least one active compound, for example, a compound of the present invention including pharmaceutically acceptable salts, pharmaceutically acceptable solvates and/or hydrates thereof and at least one pharmaceutically acceptable carrier.

The term PHARMACEUTICALLY ACCEPTABLE CARRIER or EXCIPIENT shall mean any substantially inert substance used as a diluent or vehicle for a compound of the present invention.

The phrase THERAPEUTICALLY-EFFECTIVE AMOUNT as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology) and (3) Ameliorating the disease; for example, ameliorating a disease, condition or disorder in an individual that is experiencing or displaying the pathology or symptomatology of the disease, condition or disorder (i.e., reversing the pathology and/or symptomatology).

COMPOUNDS OF THE INVENTION

One aspect of the present invention encompasses 4-oxo-4,5-dihydro-furan-2-carboxylic acid and ester derivatives as shown in Formula (I):

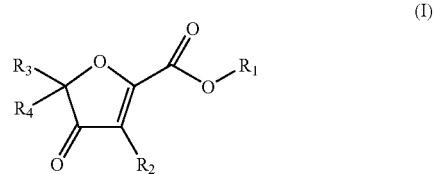

(I)

wherein:

$R_1$ is H or $C_{1-6}$ alkyl;

$R_2$ is H, halogen, $C_{1-4}$ alkyl or $C_{1-4}$ haloalkyl;

$R_3$ is aryl, $C_{3-7}$ cycloalkyl, $C_{3-7}$ cycloalkenyl, heteroaryl, $C_{3-7}$ heterocycloalkyl or $C_{3-7}$ heterocycloalkenyl wherein each are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol; and $R_4$ is selected from the group consisting of H, $C_{1-6}$ alkyl, $C_{3-6}$-cycloalkyl and $C_{1-6}$ haloalkyl wherein each are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, nitro and thiol; or a pharmaceutically acceptable salt, hydrate or solvate thereof.

In some embodiments, when $R_1$ and $R_2$ are both H and $R_4$ is methyl, then $R_3$ is not phenyl or 4-chlorophenyl.

In some embodiments, when $R_1$ and $R_2$ are both H and $R_4$ is isopropyl, then $R_3$ is not phenyl.

In some embodiments, when $R_1$ and $R_4$ are both methyl and $R_2$ is H, then $R_3$ is not phenyl.

One aspect of the present invention encompasses 4-oxo-4,5-dihydro-furan-2-carboxylic acid and ester derivatives as shown in Formula (I):

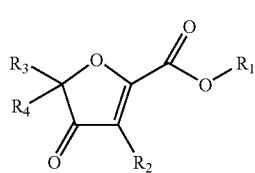

(I)

or a pharmaceutically acceptable salt, hydrate or solvate thereof, wherein:

$R_1$ is H or $C_{1-6}$ alkyl;

$R_2$ is H, halogen, $C_{1-4}$ alkyl or $C_{1-6}$ haloalkyl; and

A) $R_3$ is aryl, $C_{3-7}$ cycloalkyl, $C_{3-7}$ cycloalkenyl, heteroaryl, $C_{3-7}$ heterocycloalkyl or $C_{3-7}$ heterocycloalkenyl wherein each are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol; and $R_4$ is selected from the group consisting of H, ethyl, n-propyl, $C_{4-6}$ alkyl, $C_{3-6}$-cycloalkyl and $C_{1-6}$ haloalkyl wherein each are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, nitro and thiol; or B) $R_3$ is a substituted phenyl, 2-chlorophenyl, 3-chlorophenyl, naphthyl, $C_{3-7}$ cycloalkyl, $C_{3-7}$ cycloalkenyl, heteroaryl, $C_{3-7}$ heterocycloalkyl or $C_{3-7}$ heterocycloalkenyl wherein the 2-chlorophenyl, 3-chlorophenyl, naphthyl, $C_{3-7}$ cycloalkyl, $C_{3-7}$ cycloalkenyl, heteroaryl, $C_{3-7}$ heterocycloalkyl and $C_{3-7}$ heterocycloalkenyl are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol; and $R_4$ is selected from the group consisting of H, $C_{1-6}$ alkyl, $C_{3-6}$-cycloalkyl and $C_{1-6}$ haloalkyl wherein each are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, nitro and thiol.

The present invention also encompasses all tautomers that can exist for the compounds disclosed herein. For example, but not limited to, when $R_4$ is H, enol and keto tautomers can exist. These and other tautomers are within the scope of the invention.

The present invention also encompasses diastereomers as well as optical isomers, e.g. mixtures of enantiomers including racemic mixtures, as well as individual enantiomers and diastereomers, which arise as a consequence of structural asymmetry in certain compounds of the present invention. In some embodiments, compounds of the present invention are enriched with the R enantiomer, defined as compounds having a percent enantiomeric excess (i.e., % ee) of about 1% or greater. In some embodiments, compounds of the present invention are R. In some embodiments, compounds of the present invention are enriched with the S enantiomers. In some embodiments, compounds of the present invention are S. In some embodiments, compounds of the present invention are racemic mixtures.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids, and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent or in a mixture of the two; generally, non-aqueous media like ether, ethyl acetate, ethanol, isopropanol or acetonitrile are preferred. Lists of suitable salts are found in *Remington's Pharmaceutical Sciences,* 17th ed., Mack Publishing Company, Easton, Pa., 1985, p. 1418 and the most recent edition thereof; and *Journal of Pharmaceutical Science,* 66, 2 (1977), each of which is incorporated herein by reference in its entirety.

As used herein, "substituted" indicates that at least one hydrogen atom of the chemical group is replaced by a non-hydrogen substituent or group. When a chemical group herein is "substituted" it may have up to the full valance of substitution; for example, a methyl group can be substituted by 1, 2 or 3 substituents, a methylene group can be substituted by 1 or 2 substituents, a phenyl group can be substituted by 1, 2, 3, 4 or 5 substituents, a naphthyl group can be substituted by 1, 2, 3, 4, 5, 6 or 7 substituents, and the like.

In some embodiments, "substituted aryl" indicates an aryl group substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, nitro and thiol.

In some embodiments, the term "substituted phenyl" indicates a phenyl group substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, F, Br, I, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol.

In some embodiments, the term "substituted heteroaryl" indicates a heteroaryl group substituted with 1 to 4 groups selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, nitro and thiol.

In some embodiments, $R_1$ is $C_{1-6}$ alkyl. In some embodiments, $R_1$ is methyl or ethyl. In some embodiments, $R_1$ is methyl. In some embodiments, $R_1$ is ethyl.

In some embodiments, $R_1$ is $C_{2-6}$ alkyl.

In some embodiments, $R_1$ is H and can be represented by Formula (Ia) as shown below:

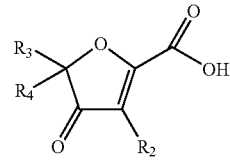

(Ia)

wherein each variable in Formula (Ia) has the same meaning as described herein, supra and infra.

In some embodiments, $R_2$ is H and can be represented by Formula (Ic) as shown below:

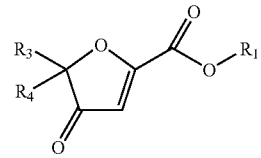

(Ic)

wherein each variable in Formula (Ic) has the same meaning as described herein, supra and infra. In some embodiments, compounds are of Formula (Ic) wherein $R_1$ is H.

In some embodiments, $R_2$ is halogen. In some embodiments, $R_2$ is F. In some embodiments, $R_2$ is Cl. In some embodiments, $R_2$ is Br.

In some embodiments, $R_2$ is $C_{1-4}$ alkyl. In one embodiment $R_2$ is methyl (i.e., —$CH_3$) and can be represented by Formula (Ie) as shown below:

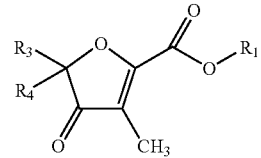

(Ie)

wherein each variable in Formula (Ie) has the same meaning as described herein, supra and infra.

In some embodiments, $R_2$ is $C_{1-4}$ haloalkyl. In some embodiments, $R_2$ is trifluoromethyl (i.e., —$CF_3$).

In some embodiments, $R_4$ is selected from the group consisting of H, $C_{1-6}$ alkyl, $C_{3-6}$-cycloalkyl and $C_{1-6}$ haloalkyl wherein each are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, nitro and thiol.

In some embodiments, $R_4$ is selected from the group consisting of H, ethyl, n-propyl, $C_{4-6}$ alkyl, $C_{3-6}$ cycloalkyl and $C_{1-6}$ haloalkyl wherein each are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylamino, hydroxyl, nitro and thiol.

In some embodiments, $R_4$ is $C_{1-6}$ alkyl. In some embodiments, $R_4$ is methyl. In some embodiments, $R_4$ is ethyl.

In some embodiments, $R_4$ is $C_{1-6}$ haloalkyl. In some embodiments, $R_4$ is trifluoromethyl (i.e., —$CF_3$), difluoromethyl (i.e., —$CHF_2$) or fluoromethyl (i.e., —$CH_2F$). In some embodiments, $R_4$ is trifluoromethyl. In some embodiments, $R_4$ is pentafluoroethyl (i.e., —$CF_2CF_3$), 2,2,2-trifluoroethyl (i.e., —$CH_2CF_3$) or 1,1-difluoroethyl (i.e., —$CF_2CH_3$).

In some embodiments, $R_3$ is aryl, $C_{3-7}$ cycloalkyl, $C_{3-7}$ cycloalkenyl, heteroaryl, $C_{3-7}$ heterocycloalkyl or $C_{3-7}$ heterocycloalkenyl wherein each are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol.

In some embodiments, $R_3$ is a substituted phenyl, 2-chlorophenyl, 3-chlorophenyl, naphthyl, $C_{3-7}$ cycloalkyl, $C_{3-7}$ cycloalkenyl, heteroaryl, $C_{3-7}$ heterocycloalkyl or $C_{3-7}$ heterocycloalkenyl wherein the 2-chlorophenyl, 3-chlorophenyl, naphthyl, $C_{3-7}$ cycloalkyl, $C_{3-7}$ cycloalkenyl, heteroaryl, $C_{3-7}$ heterocycloalkyl and $C_{3-7}$ heterocycloalkenyl are optionally substituted with 1 to 5 substituents selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol.

In some embodiments, $R_3$ is substituted phenyl, 3-chlorophenyl, $C_{3-7}$ cycloalkyl, $C_{3-7}$ cycloalkenyl or heteroaryl, wherein said 3-chlorophenyl, $C_{3-7}$ cycloalkyl, $C_{3-7}$ cycloalkenyl and heteroaryl are optionally substituted with 1 to 5 substituents selected from the group consisting of $C_{2-6}$ alkenyl, $C_{1-6}$ alkoxy, $C_{1-6}$ alkyl, aryl, cyano, halogen, $C_{1-6}$ haloalkyl and heteroaryl.

In some embodiments, $R_3$ is aryl optionally substituted with 1 to 5 substituents. In some embodiments, compounds can be represented by Formula (Ig) as shown below:

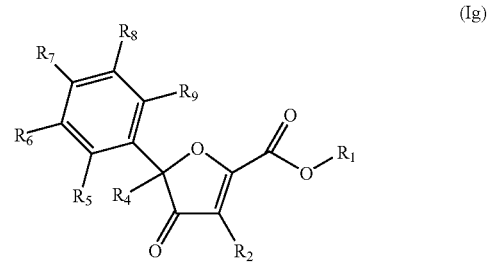

wherein $R_1$, $R_2$ and $R_4$ are as defined herein supra and infra and $R_5$ to $R_9$ are each independently selected from the group consisting of H, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol.

In some embodiments, compounds of the present invention are of Formula (Ig) wherein $R_1$, $R_2$ and $R_4$ are as defined herein supra and infra, $R_5$, $R_6$, $R_8$ and $R_9$ are each independently selected from the group consisting of H, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol; and $R_7$ is selected from the group consisting of H, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, F, Br, I, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol.

In some embodiments, $R_3$ is selected from the group consisting of biphenyl-3-yl, 3-thiophen-2-yl-phenyl, 3-bromophenyl, 3-iodo-phenyl, 3-chloro-phenyl, 3-fluoro-phenyl, 3,5-difluoro-phenyl, m-tolyl, 3-ethyl-phenyl, 3-trifluoromethyl-phenyl, 4-fluoro-phenyl, 2-fluoro-phenyl, 3,4-difluorophenyl, 2,4-difluoro-phenyl, 2,6-difluoro-phenyl, 2,5-dichloro-phenyl, 3-methoxy-phenyl, 3,5-dichloro-phenyl, 3-cyano-phenyl, 3-propenyl-phenyl, 3-hex-1-enyl-phenyl and 3-vinyl-phenyl.

In some embodiments, when $R_5$, $R_6$, $R_8$ and $R_9$ are all H, then $R_7$ is not Cl.

In some embodiments, at least one $R_5$, $R_6$, $R_7$, $R_8$ and $R_9$ is a group other than H.

In some embodiments, $R_3$ is phenyl optionally substituted with $C_{1-6}$ alkyl, aryl, substituted aryl, halogen, $C_{1-6}$ haloalkyl, heteroaryl or substituted heteroaryl.

In some embodiments, $R_3$ is phenyl optionally substituted with $C_{1-6}$ alkyl, aryl, halogen, $C_{1-6}$ haloalkyl or heteroaryl. In some embodiments, $R_3$ is phenyl optionally substituted with methyl, ethyl, phenyl, F, Cl, Br, I, trifluoromethyl or thiophene.

In some embodiments, $R_3$ is a substituted phenyl. In some embodiments, $R_3$ is a phenyl substituted with 1 to 5 substituents selected from the group consisting of $C_{1-6}$ alkyl, aryl, substituted aryl, F, Br, I, $C_{1-6}$ haloalkyl, heteroaryl and substituted heteroaryl. In some embodiments, the phenyl is substituted with 1 to 5 substituents selected from the group consisting of methyl, ethyl, phenyl, F, Br, I, trifluoromethyl and thiophene.

In some embodiments, $R_3$ is 2-chlorophenyl or 3-chlorophenyl wherein each is optionally substituted with 1 to 4 substituents selected from the group consisting of $C_{1-6}$ alkyl, aryl, substituted aryl, halogen, $C_{1-6}$ haloalkyl, heteroaryl and substituted heteroaryl. In some embodiments, $R_3$ is 2-chlorophenyl or 3-chlorophenyl wherein each is optionally substituted with 1 to 5 substituents selected from the group consisting of methyl, ethyl, phenyl, F, Cl, Br, trifluoromethyl and thiophene.

In some embodiments, $R_3$ is $C_{3-7}$ cycloalkenyl optionally substituted with 1 to 5 substituents. In some embodiments, $R_3$ is cyclopentyl optionally substituted with 1 to 5 substituents. In some embodiments, $R_3$ is cyclohexenyl optionally substituted with 1 to 5 substituents.

In some embodiments, $R_3$ is heteroaryl optionally substituted with 1 to 4 substituents. In some embodiments, $R_3$ is heteroaryl optionally substituted with 1 to 4 substituents each independently selected from the group consisting of $C_{1-6}$ alkyl, halogen and $C_{1-6}$ haloalkyl. In some embodiments, $R_3$ is heteroaryl optionally substituted with 1 to 4 substituents each independently selected from the group consisting of methyl, ethyl, F, Cl, Br, I and trifluoromethyl.

In some embodiments, $R_3$ is a 5-membered heteroaryl optionally substituted with 1 to 4 substituents. In some embodiments, $R_3$ is a thienyl and can be represented by Formula (Ii) as shown below:

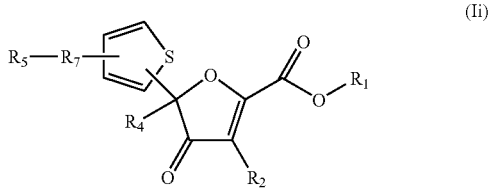

(Ii)

wherein $R_1$, $R_2$ and $R_4$ in Formula (Ii) are as defined herein supra and infra and $R_5$ to $R_7$ are each independently selected from the group consisting of H, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol. In some embodiments, $R_3$ is thienyl optionally substituted with $C_{1-6}$ alkyl, halogen or $C_{1-6}$ haloalkyl. In some embodiments, $R_3$ is thienyl optionally substituted with methyl, ethyl, F, Cl, Br, I or trifluoromethyl.

In some embodiments, $R_3$ is selected from the group consisting of thiophen-3-yl, thiophen-2-yl, 4-bromo-thiophen-2-yl, 5-methyl-thiophen-2-yl, 5-chloro-thiophen-2-yl, 5-bromo-thiophen-3-yl, 5-chloro-thiophen-3-yl, 4-bromo-5-methyl-thiophen-2-yl, pyridin-3-yl, furan-2-yl, 4-methyl-thiophen-2-yl and 5-methyl-thiophen-3-yl.

In some embodiments, $R_3$ is thien-2-yl optionally substituted with 1 to 3 substituents and can be represented by Formula (Ik) as shown below:

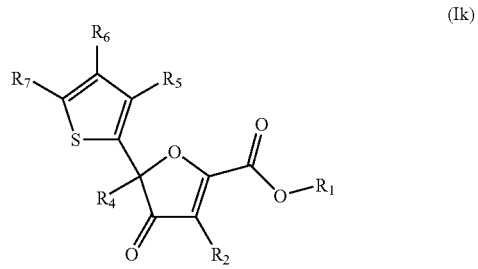

(Ik)

wherein $R_1$, $R_2$ and $R_4$ in Formula (Ik) are as defined herein supra and infra and $R_5$ to $R_7$ are each independently selected from the group consisting of H, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol. In some embodiments, $R_5$ to $R_7$ are each independently selected from the group consisting of H, $C_{1-6}$ alkyl, halogen and $C_{1-6}$ haloalkyl. In some embodiments, $R_5$ to $R_7$ are each independently selected from the group consisting of H, methyl, ethyl, F, Cl, Br, I or trifluoromethyl.

In some embodiments, $R_3$ is selected from the group consisting of cyclohex-1-enyl, cyclopent-1-enyl and cyclopentyl.

In some embodiments,
$R_1$ is H;
$R_2$ is H;
$R_4$ is $C_{1-6}$ alkyl or $C_{1-6}$ haloalkyl; and
$R_3$ is substituted phenyl, 3-chlorophenyl, $C_{3-7}$ cycloalkyl, $C_{3-7}$ cycloalkenyl or heteroaryl, wherein said 3-chlorophenyl, $C_{3-7}$ cycloalkyl, $C_{3-7}$ cycloalkenyl and heteroaryl are optionally substituted with 1 to 5 substituents selected from the group consisting of $C_{2-6}$ alkenyl, $C_{1-6}$ alkoxy, $C_{1-6}$ alkyl, aryl, cyano, halogen, $C_{1-6}$ haloalkyl and heteroaryl.

In some embodiments,
$R_1$ is H;
$R_2$ is H;
$R_4$ is methyl, ethyl or trifluoromethyl; and
$R_3$ is selected from the group consisting of biphenyl-3-yl, 3-thiophen-2-yl-phenyl, 3-bromo-phenyl, 3-iodo-phenyl, 3-chloro-phenyl, 3-fluoro-phenyl, 3,5-difluoro-phenyl, m-tolyl, 3-ethyl-phenyl, 3-trifluoromethyl-phenyl, 3,4-difluoro-phenyl, 2,4-difluoro-phenyl, 2,6-difluoro-phenyl, 2,5- dichloro-phenyl, 3-methoxy-phenyl, 3,5-dichloro-phenyl, 3-cyano-phenyl, 3-propenyl-phenyl, 3-hex-1-enyl-phenyl and 3-vinyl-phenyl.

In some embodiments, $R_1$ is H;

$R_2$ is H;

$R_4$ is methyl, ethyl or trifluoromethyl; and $R_3$ is thienyl optionally substituted with $C_{1-6}$ alkyl or halogen.

In some embodiments, $R_1$ is H;

$R_2$ is H;

$R_4$ is methyl, ethyl or trifluoromethyl; and $R_3$ is selected from the group consisting of thiophen-3-yl, thiophen-2-yl, 4-bromo-thiophen-2-yl, 5-methyl-thiophen-2-yl, 5-chloro-thiophen-2-yl, 5-bromo-thiophen-3-yl, 5-chloro-thiophen-3-yl, 4-bromo-5-methyl-thiophen-2-yl, pyridin-3-yl, furan-2-yl, 4-methyl-thiophen-2-yl and 5-methyl-thiophen-3-yl.

In some aspects of each embodiment of the present invention, compounds have in vitro $EC_{50}$ values at the RUP25 receptor of less than ½, ⅓, ¼, or ⅕ of the in vitro $EC_{50}$ value at the RUP25 receptor for acifran.

Methods for Making the Compounds of the Invention

Synthesis of Compounds of Formula (I)

The compounds of the invention can be made using conventional organic syntheses and/or by the following illustrative methods.

In one embodiment of the present invention is a novel synthetic process for the preparation of compounds of Formula (I). The compounds of the present invention can be prepared according to this novel process utilizing a variety of starting materials that are either commercially available or readily prepared by synthetic regimes that would be familiar to ones skilled in the art. In the illustrated syntheses outlined below, the labeled substituents have the same identifications as set out in the definitions of the compound described above for Formula (I) and throughout this disclosure.

One method that can be used to prepare compounds of the present invention, wherein $R_2$ is H, $C_{1-4}$ is alkyl or $C_{1-4}$ haloalkyl, utilizes intermediates derived from Compound (B) as illustrated in Reaction Scheme (1) below:

Reaction Scheme (1)

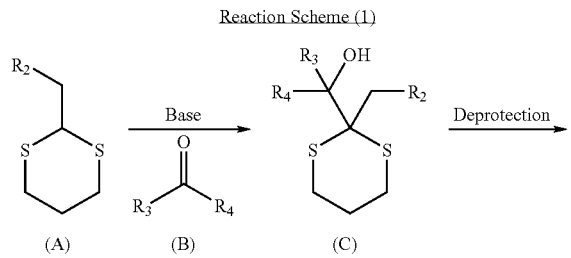

-continued

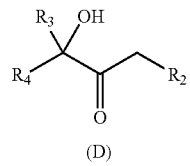

(D)

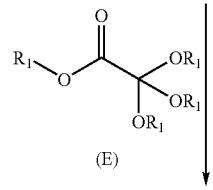

(E)

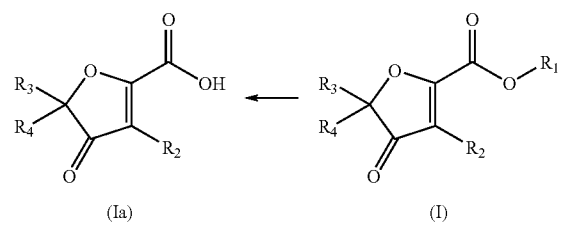

(Ia)            (I)

Compounds of the invention can be prepared via the intermediates as shown in the above reaction scheme. By selecting the desired Compound (B) a variety of $R_3$ and $R_4$ groups can be introduced into the compounds of the invention. Compound (B) can either be obtained via commercial sources or prepared by methods known to organic chemists. Compound (B) can be reacted with the anion of Dithiane (A) to provide Hydroxydithiane (C). Bases of appropriate strength to form the anion are known in the art, for example, but not limited to, "$C_{1-10}$ alkyl lithium bases" such as methyl lithium, ethyl lithium, propyl lithium, n-butyl lithium, sec-butyl lithium, t-butyl lithium, and the like; "$C_{1-10}$ alkylamide bases" such as lithium diisopropylamide (i.e., LDA), and the like; "metal $C_{1-10}$ alkyldisilazane bases" such as lithium hexamethyldisilazane, sodium hexamethyldisilazane, potassium hexamethyldisilazane and like bases. Hydroxydithiane (C) is deprotected to provide Hydroxyketone (D). Suitable deprotecting reagents, include but not limited to, mercury-(II)-inorganic salts such as, $Hg(ClO_4)_2$, HgO, $HgCl_2$, and the like; deprotecting reagents can be used either separately or in combination with other deprotecting reagent. Hydroxyketone (D) is reacted with Orthoester (E) in the presence of a base which can be treated directly with an acid to give Compounds of Formula (I). Suitable bases include alkali metal alkoxides, for example, sodium methoxide, sodium ethoxide, potassium ethoxide, potassium t-butoxide, and the like; metal hydride bases, for example, NaH, KH, LiH, and the like; and the bases as described above. Compounds of Formula (I), where $R_1$ is $C_{1-6}$ alkyl, can be converted to Acid (Ia) via methods known in the art, for example but not limited to, hydrolysis, under basic conditions such as KOH, NaOH, LiOH, $K_2CO_3$, and the like; or under acidic conditions such as HCl, HBr, HI, $H_2SO_4$, $H_3PO_4$, and the like.

Alternately, compounds of the present invention can be prepared utilizing the Reaction Scheme (2) as illustrated below:

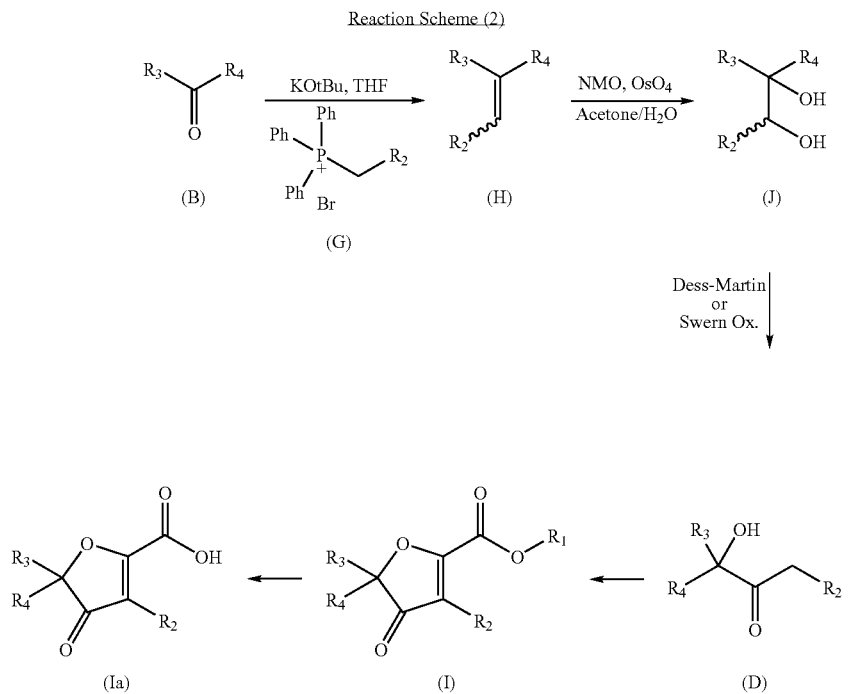

In a similar manner as described herein, supra, by selecting the desired Compound (B) a variety of $R_3$ and $R_4$ groups can be introduced into the compounds of the invention. Compound (B) can be converted to Olefin (H) via an olefination reaction known in the art, for example, Wittig Reaction, as shown in the Reaction Scheme (2), Peterson Olefination, a modified Horner-Wadsworth-Emmons Reaction, and the like. Suitable bases include the bases of appropriate strength to form the anion as known in the art for a particular olefination reaction, for example, but not limited to, "$C_{1-10}$ alkyl lithium bases" such as methyl lithium, ethyl lithium, propyl lithium, n-butyl lithium, sec-butyl lithium, t-butyl lithium, and the like; "$C_{1-10}$ alkylamide bases" such as lithium diisopropylamide (i.e., LDA), and the like; "metal $C_{1-10}$ alkyldisilazane bases" such as lithium hexamethyldisilazane, sodium hexamethyldisilazane, potassium hexamethyldisilazane; metal $C_{1-10}$ alkoxide, such as potassium t-butoxide; and like bases. Olefin (H) can be oxidized to provide Diol (J). Suitable oxidizing reagents include but not limited to, $OsO_4$, and the like. Diol (J) is subsequently oxidized to give Ketone (D). Suitable oxidation reagents/reactions include, Dess-Martin, Swern Oxidation, Corey Oxidation using DMS/NCS and suitable procedures described in Hudlicky, M., *Oxidation in Organic Chemistry*, ACS Monograph 186 (1990), incorporated herein by reference in its entirety. Ketone (D) is converted to compounds of the invention in a similar manner as described above in Reaction Scheme (1).

One method that can be used to prepare compounds of the present invention, wherein $R_2$ is halogen, utilizes compounds of Formula (Ic), wherein $R_1$ is $C_{1-6}$ alkyl, as illustrated in Reaction Scheme (3) below:

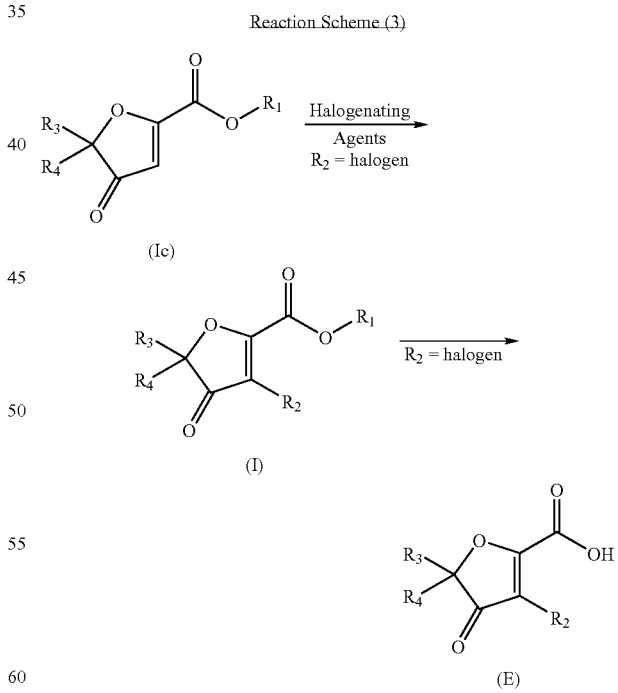

Compounds (Ic) can be halogenated to give Compounds of Formula (I), where $R_2$ is halogen, using a variety of halogenating agents. Suitable halogenating agents include, but not limited to, $F_2$, $Cl_2$, $Br_2$, $I_2$, various known fluorinating agents (such as, Selectfluor™, and the like), NCS, NBS, NIS, $I_2$ and an Ag salt (such as, AgF), and the like. Compounds of Formula (I), where $R_2$ is halogen, can be converted to the corresponding carboxylic acids (i.e., compounds of Formula (Ia) where $R_2$ is halogen) in an analoguous manner as described above.

Compounds of the present invention can be resolved into pure or substantially pure enantiomers using methods known in the art. One particular method is illustrated in Reation Scheme (4) as shown below:

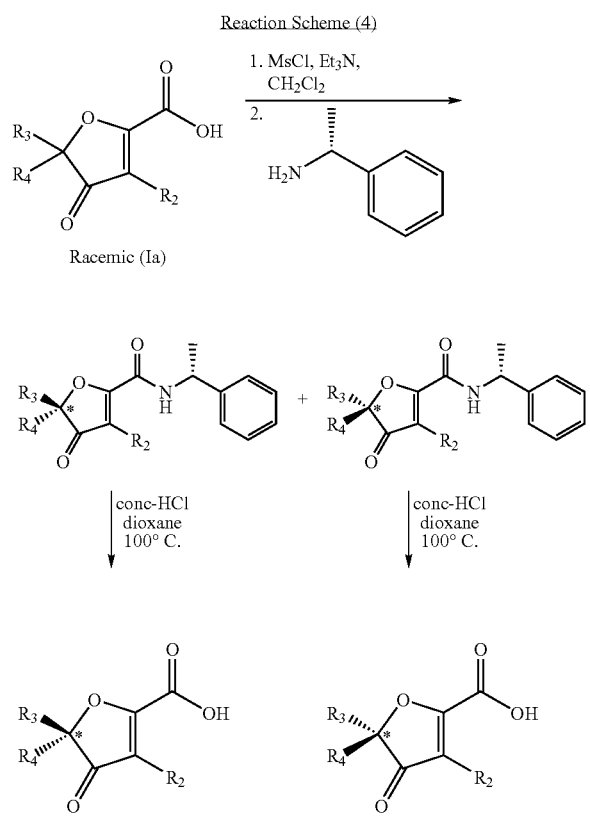

Acid (Ia) can be coupled to a chiral amine to form the corresponding diasteomeric amide mixture. This mixture can be separated using methods known in the art, such as, chromatography, recrystallization, and the like. Each diasteromeric acid is independently hydrolyzed to provide the separate enantiomer. One particularly useful chiral amine is (+)-α-methylbenzylamine as shown in Example 10, infra.

The various organic group transformations and protecting groups utilized herein can be performed by a number of procedures other than those described above. References for other synthetic procedures that can be utilized for the preparation of intermediates or compounds disclosed herein can be found in, for example, Smith, M. B.; and March, J., *Advanced Organic Chemistry*, 5th Edition, Wiley-Interscience (2001); Larock, R. C., *Comprehensive Organic Transformations, A Guide to Functional Group Preparations*, 2nd Edition, VCH Publishers, Inc. (1999) or Wuts, P. G. M.; Greene, T. W.; *Protective Groups in Organic Synthesis*, 3rd Edition, John Wiley and Sons, (1999), all three citations incorporated herein by reference in their entirety.

Compounds of the invention may have one or more chiral centers and therefore exist as enantiomers or diastereomers. The invention is understood to extend to all such enantiomers, diastereomers and mixtures thereof, including racemates. Formula (I) and the formulae described herein, supra, are intended to represent all individual isomers and mixtures thereof, unless stated or shown otherwise.

Racemic mixtures can be resolved into the optical pure enantiomers by known methods, for example, by separation of diastereomeric salts thereof with an optically active acid and liberating the optically active amine compound by treatment with a base. Similarly, racemic mixtures can be resolved by separation of diastereomeric salts thereof with an optically active base and liberating the optically active acid compound by treatment with an acid. Another method for resolving racemates into the optical pure enantiomers is based upon chromatography on an optically active matrix or chiral support. Certain racemic compounds of the present invention can thus be resolved into their optical antipodes, e.g., by fractional crystallization of d- or l-(tartrates, mandelates or camphorsulphonate) salts for example. The compounds of the present invention may also be resolved by the formation of diastereomeric amides or esters by reaction of the compounds of the present invention with an optically active amine or alcohol such as that derived from (+) or (–) α-methylbenzylamine or the like, separated via fractional recrystallization, chiral chromatography or similar method and subsequently hydrolyzed.

Additional methods for the resolution of optical isomers known to those skilled in the art can be used and will be apparent to the average worker skilled in the art. Such methods include those discussed by J. Jaques, A. Collet and S. Wilen in "Enantiomers, Racemates and Resolutions", John Wiley and Sons, New York (1981).

It is understood that the chemistry described herein is representative and is not intended to be limiting in any manner.

Representative compounds of the invention are shown below in TABLE A.

The compounds disclosed in TABLE A, TABLE B and certain intermediates within the Examples, infra, were named according to AutoNom Version 2.2 found in Chem Draw Ultra Version 7.0 or AutoNom 2000 found in Isis Draw.

TABLE A

| Cmpd # | Structure | Chemical Name |
|---|---|---|
| 1 | 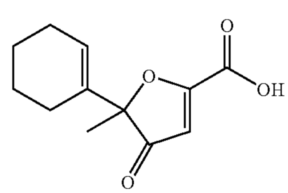 | 5-Cyclohex-1-enyl-5-methyl-4-oxo-4,5-dihydro-furan-2-carboxylic acid |

TABLE A-continued

| Cmpd # | Structure | Chemical Name |
| --- | --- | --- |
| 2 | 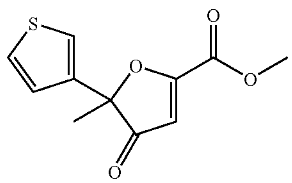 | 5-Methyl-4-oxo-5-thiophen-3-yl-4,5-dihydro-furan-2-carboxylic acid methyl ester |
| 3 | 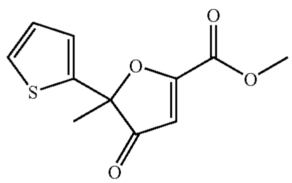 | 5-Methyl-4-oxo-5-thiophen-2-yl-4,5-dihydro-furan-2-carboxylic acid methyl ester |
| 4 | 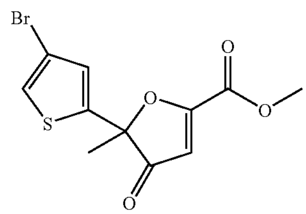 | 5-(4-Bromo-thiophen-2-yl)-5-methyl-4-oxo-4,5-dihydro-furan-2-carboxylic acid methyl ester |
| 5 | 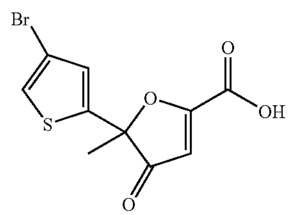 | 5-(4-Bromo-thiophen-2-yl)-5-methyl-4-oxo-4,5-dihydro-furan-2-carboxylic acid |
| 6 | 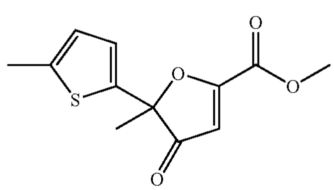 | 5-Methyl-5-(5-methyl-thiophen-2-yl)-4-oxo-4,5-dihydro-furan-2-carboxylic acid methyl ester |
| 7 | 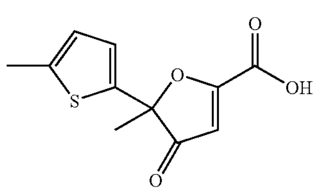 | 5-Methyl-5-(5-methyl-thiophen-2-yl)-4-oxo-4,5-dihydro-furan-2-carboxylic acid |
| 8 | 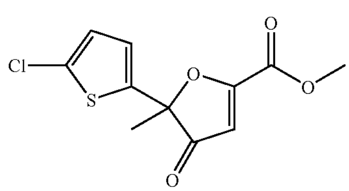 | 5-(5-Chloro-thiophen-2-yl)-5-methyl-4-oxo-4,5-dihydro-furan-2-carboxylic acid methyl ester |
| 9 | 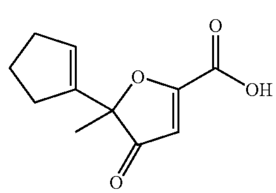 | 5-Cyclopent-1-enyl-5-methyl-4-oxo-4,5-dihydro-furan-2-carboxylic acid |

TABLE A-continued

| Cmpd # | Structure | Chemical Name |
|---|---|---|
| 10 | 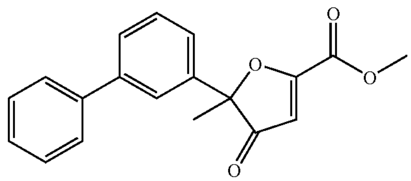 | 5-Biphenyl-3-yl-5-methyl-4-oxo-4,5-dihydro-furan-2-carboxylic acid methyl ester |
| 11 | 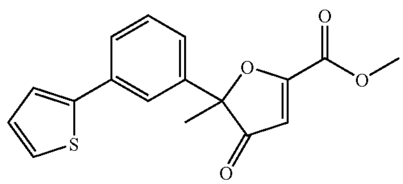 | 5-Methyl-4-oxo-5-(3-thiophen-2-yl-phenyl)-4,5-dihydra-furan-2-carboxylic acid methyl ester |
| 12 | 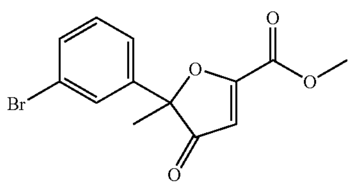 | 5-(3-Bromo-phenyl)-5-methyl-4-oxo-4,5-dihydro-furan-2-carboxylic acid methyl ester |
| 13 | 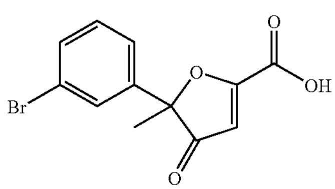 | 5-(3-Bromo-phenyl)-5-methyl-4-oxo-4,5-dihydro-furan-2-carboxylic acid |
| 14 | 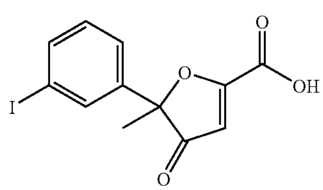 | 5-(3-Iodo-phenyl)-5-methyl-4-oxo-4,5-dihydro-furan-2-carboxylic acid |
| 15 | 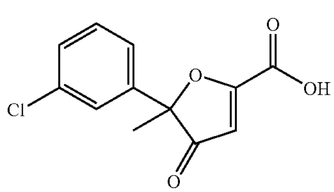 | 5-(3-Chloro-phenyl)-5-methyl-4-oxo-4,5-dihydro-furan-2-carboxylic acid |
| 16 | 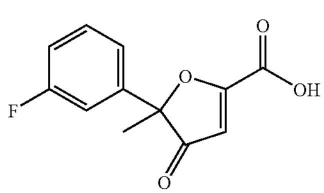 | 5-(3-Fluoro-phenyl)-5-methyl-4-oxo-4,5-dihydro-furan-2-carboxylic acid |

TABLE A-continued

| Cmpd # | Structure | Chemical Name |
|---|---|---|
| 17 | 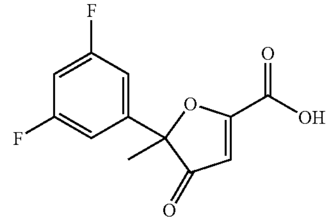 | 5-(3,5-Difluoro-phenyl)-5-methyl-4-oxo-4,5-dihydro-furan-2-carboxylic acid |
| 18 | 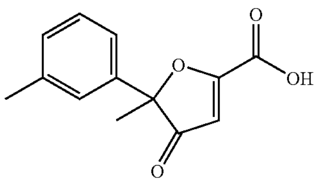 | 5-Methyl-4-oxo-5-m-tolyl-4,5-dihydro-furan-2-carboxylic acid |
| 19 | 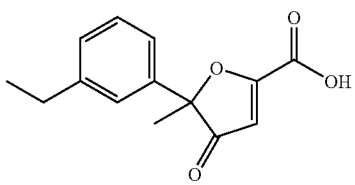 | 5-(3-Ethyl-phenyl)-5-methyl-4-oxo-4,5-dihydro-furan-2-carboxylic acid |
| 20 | 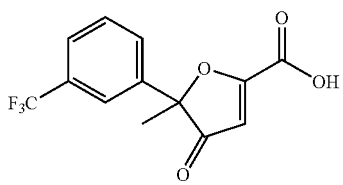 | 5-Methyl-4-oxo-5-(3-trifluoromethyl-phenyl)-4,5-dihydro-furan-2-carboxylic acid |
| 21 | 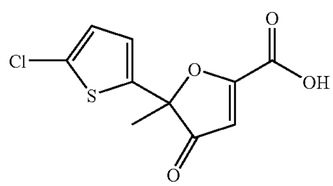 | 5-(5-Chloro-thiophen-2-yl)-5-methyl-4-oxo-4,5-dihydro-furan-2-carboxylic acid |
| 22 | 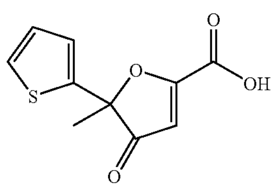 | 5-Methyl-4-oxo-5-thiophen-2-yl-4,5-dihydro-furan-2-carboxylic acid |
| 23 | 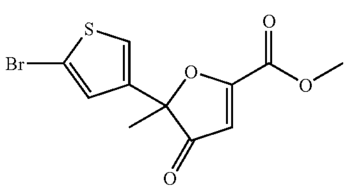 | 5-(5-Bromo-thiophen-3-yl)-5-methyl-4-oxo-4,5-dihydro-furan-2-carboxylic acid methyl ester |
| 24 | 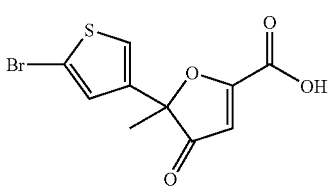 | 5-(5-Bromo-thiophen-3-yl)-5-methyl-4-oxo-4,5-dihydro-furan-2-carboxylic acid |

TABLE A-continued

| Cmpd # | Structure | Chemical Name |
|---|---|---|
| 25 | 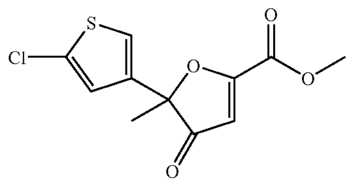 | 5-(5-Chloro-thiophen-3-yl)-5-methyl-4-oxo-4,5-dihydro-furan-2-carboxylic acid methyl ester |
| 26 | 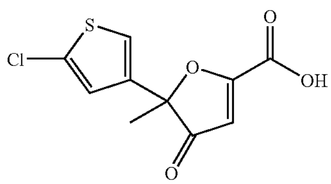 | 5-(5-Chloro-thiophen-3-yl)-5-methyl-4-oxo-4,5-dihydro-furan-2-carboxylic acid |
| 27 | 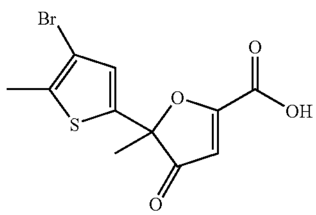 | 5-(4-Bromo-5-methyl-thiophen-2-yl)-5-methyl-4-oxo-4,5-dihydro-furan-2-carboxylic acid |
| 28 | 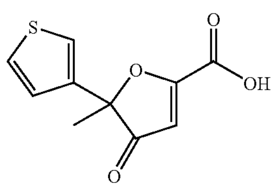 | 5-Methyl-4-oxo-5-thiophen-3-yl-4,5-dihydro-furan-2-carboxylic acid |

Representative compounds of the invention are shown below in TABLE B.

TABLE B

| Cmpd # | Chemical Structure | Chemical Name |
|---|---|---|
| 29 | 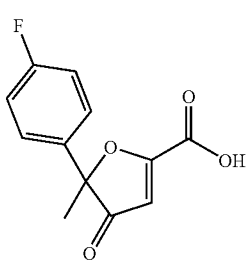 | 5-(4-Fluoro-phenyl)-5-methyl-4-oxo-4,5-dihydro-furan-2-carboxylic acid |
| 30 | 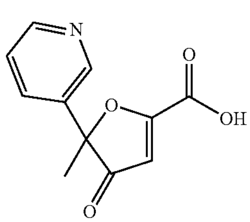 | 5-Methyl-4-oxo-5-pyridin-3-yl-4,5-dihydro-furan-2-carboxylic acid |

TABLE B-continued

| Cmpd # | Chemical Structure | Chemical Name |
|---|---|---|
| 31 | 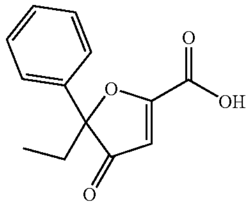 | 5-Ethyl-4-oxo-5-phenyl-4,5-dihydro-furan-2-carboxylic acid |
| 32 | 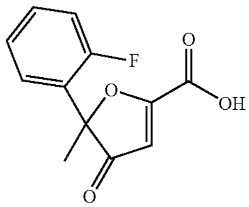 | 5-(2-Fluoro-phenyl)-5-methyl-4-oxo-4,5-dihydro-furan-2-carboxylic acid |
| 33 | 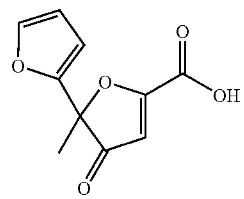 | 2-Methyl-3-oxo-2,3-dihydro-[2,2']bifuranyl-5-carboxylic acid |
| 34 | 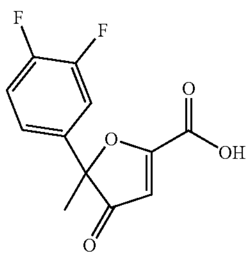 | 5-(3,4-Difluoro-phenyl)-5-methyl-4-oxo-4,5-dihydro-furan-2-carboxylic acid |
| 35 | 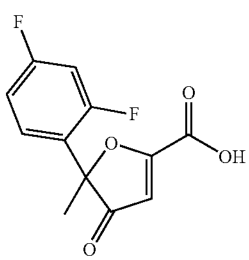 | 5-(2,4-Difluoro-phenyl)-5-methyl-4-oxo-4,5-dihydro-furan-2-carboxylic acid |
| 36 | 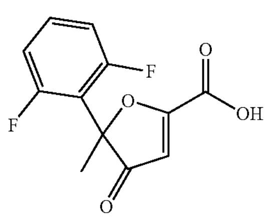 | 5-(2,6-Difluoro-phenyl)-5-methyl-4-oxo-4,5-dihydro-furan-2-carboxylic acid |
| 37 | 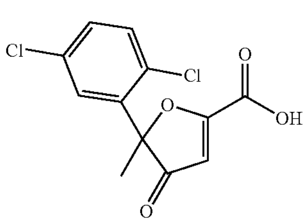 | 5-(2,5-Dichloro-phenyl)-5-methyl-4-oxo-4,5-dihydro-furan-2-carboxylic acid |

TABLE B-continued

| Cmpd # | Chemical Structure | Chemical Name |
|---|---|---|
| 38 | 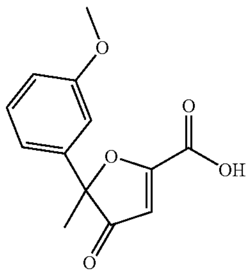 | 5-(3-Methoxy-phenyl)-5-methyl-4-oxo-4,5-dihydro-furan-2-carboxylic acid |
| 39 | 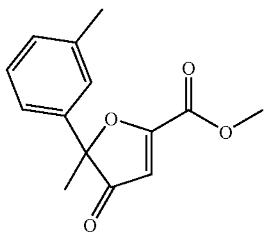 | 5-Methyl-4-oxo-5-m-tolyl-4,5-dihydro-furan-2-carboxylic acid methyl ester |
| 40 | 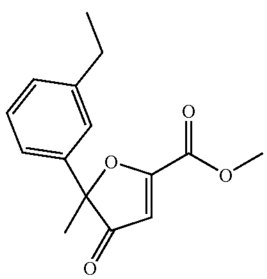 | 5-(3-Ethyl-phenyl)-5-methyl-4-oxo-4,5-dihydro-furan-2-carboxylic acid methyl ester |
| 41 | 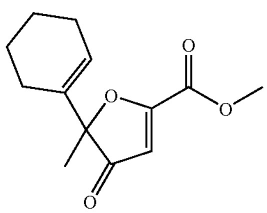 | 5-Cyclohex-1-enyl-5-methyl-4-oxo-4,5-dihydro-furan-2-carboxylic acid methyl ester |
| 42 | 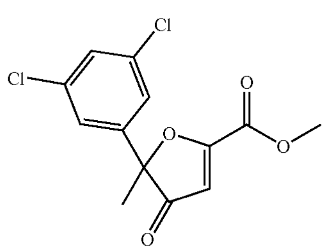 | 5-(3,5-Dichloro-phenyl)-5-methyl-4-oxo-4,5-dihydro-furan-2-carboxylic acid methyl ester |
| 43 | 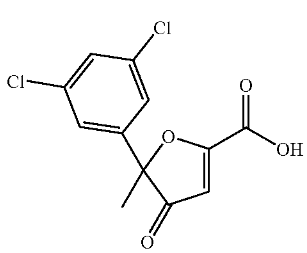 | 5-(3,5-Dichloro-phenyl)-5-methyl-4-oxo-4,5-dihydro-furan-2-carboxylic acid |

TABLE B-continued

| Cmpd # | Chemical Structure | Chemical Name |
|---|---|---|
| 44 | 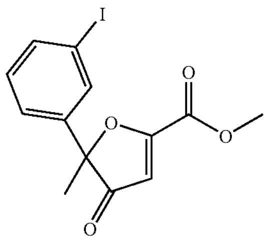 | 5-(3-Iodo-phenyl)-5-methyl-4-oxo-4,5-dihydro-furan-2-carboxylic acid methyl ester |
| 45 | 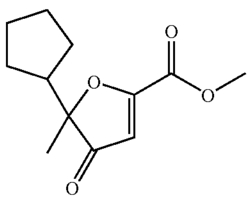 | 5-Cyclopentyl-5-methyl-4-oxo-4,5-dihydro-furan-2-carboxylic acid methyl ester |
| 46 | 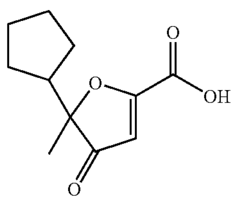 | 5-Cyclopentyl-5-methyl-4-oxo-4,5-dihydro-furan-2-carboxylic acid |
| 47 | 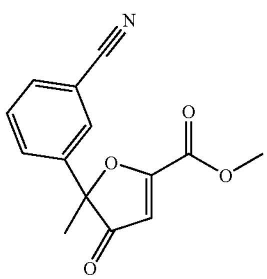 | 5-(3-Cyano-phenyl)-5-methyl-4-oxo-4,5-dihydro-furan-2-carboxylic acid methyl ester |
| 48 | 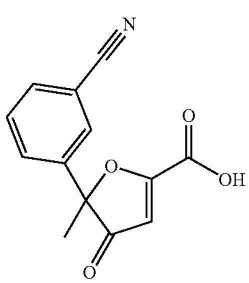 | 5-(3-Cyano-phenyl)-5-methyl-4-oxo-4,5-dihydro-furan-2-carboxylic acid |
| 49 | 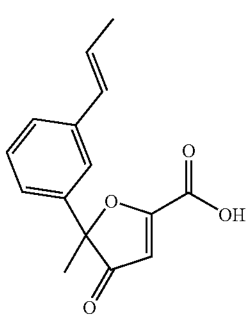 | 5-Methyl-4-oxo-5-{((E)-3-propenyl)-phenyl]-4,5-dihydro-furan-2-carboxylic acid |

TABLE B-continued

| Cmpd # | Chemical Structure | Chemical Name |
| --- | --- | --- |
| 50 | 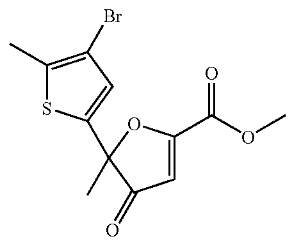 | 5-(4-Bromo-5-methyl-thiophen-2-yl)-5-methyl-4-oxo-4,5-dihydro-furan-2-carboxylic acid methyl ester |
| 51 | 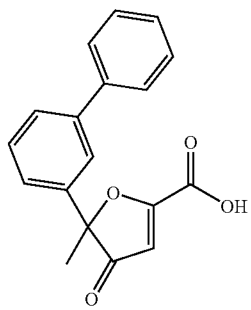 | 5-Biphenyl-3-yl-5-methyl-4-oxo-4,5-dihydro-furan-2-carboxylic acid |
| 52 | 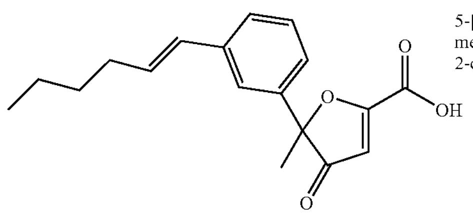 | 5-[((E)-3-Hex-1-enyl)-phenyl]-5-methyl-4-oxo-4,5-dihydro-furan-2-carboxylic acid |
| 53 | 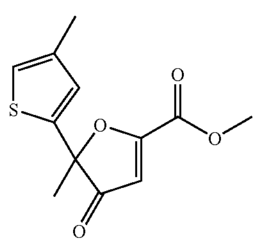 | 5-Methyl-5-(4-methyl-thiophen-2-yl)-4-oxo-4,5-dihydro-furan-2-carboxylic acid methyl ester |
| 54 | 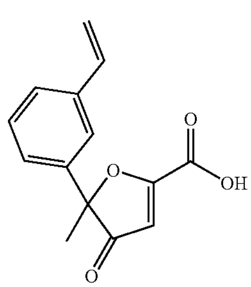 | 5-Methyl-4-oxo-5-(3-vinyl-phenyl)-4,5-dihydro-furan-2-carboxylic acid |
| 55 | 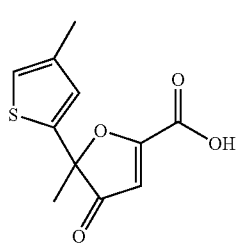 | 5-Methyl-5-(4-methyl-thiophen-2-yl)-4-oxo-4,5-dihydro-furan-2-carboxylic acid |

TABLE B-continued

| Cmpd # | Chemical Structure | Chemical Name |
| --- | --- | --- |
| 56 | 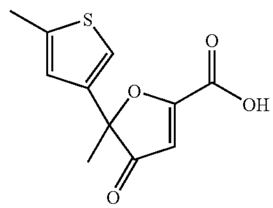 | 5-Methyl-5-(5-methyl-thiophen-3-yl)-4-oxo-4,5-dihydro-furan-2-carboxylic acid |
| 57 | 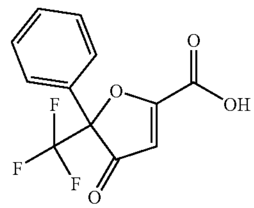 | 4-Oxo-5-phenyl-5-trifluoromethyl-4,5-dihydro-furan-2-carboxylic acid |

Methods and Uses

Compounds of the present invention can modulate the activity of the RUP25 receptor. The term "modulate" is meant to refer to the ability to increase or decrease activity of the receptor. In some embodiments, compounds of the invention can be used in methods of modulating a RUP25 receptor by contacting the receptor with any one or more of the compound as described herein. In still other embodiments, compounds of the invention can be used in methods of modulating a RUP25 receptor for the treatment of a metabolic-related disorder in an individual in need of such modulation comprising contacting the receptor with a therapeutically-effective amount of a compound of Formula (I). In some embodiments, compounds of the invention increase activity of the RUP25 receptor. In further embodiments, compounds of the invention are agonists of the RUP25 receptor. The term "agonist", as used herein, refers to agents that can stimulate activity of the receptor (i.e., activate), like the RUP25 receptor. In some embodiments, compounds of the invention are partial agonists of the RUP25 receptor.

Another aspect of the present invention pertains to methods of treatment of a metabolic-related disorder comprising administering to an individual in need of such treatment a therapeutically-effective amount of a compound of Formula (I).

Another aspect of the present invention pertains to methods of raising HDL in an individual comprising administering to the individual a therapeutically-effective amount of a compound of Formula (I).

Another aspect of the present invention pertains to compounds of Formula (I), as described herein, for use in a method of treatment of the human or animal body by therapy.

Another aspect of the present invention pertains to compounds of Formula (I), as described herein, for use in a method of treatment of a metabolic-related disorder of the human or animal body by therapy.

Another aspect of the present invention pertains to compounds of Formula (I), as described herein, for use in a method of treatment of a metabolic-related disorder of the human or animal body by therapy wherein the metabolic-related disorder is selected from the group consisting of dyslipidemia, atherosclerosis, coronary heart disease, insulin resistance, obesity, impaired glucose tolerance, atheromatous disease, hypertension, stroke, Syndrome X, heart disease and type 2 diabetes.

Another aspect of the present invention pertains to compounds of Formula (I), as described herein, for use in a method of treatment of a metabolic-related disorder of the human or animal body by therapy wherein the metabolic-related disorder is selected from the group consisting of dyslipidemia, atherosclerosis, coronary heart disease, insulin resistance and type 2 diabetes.

Another aspect of the present invention pertains to compounds of Formula (I), as described herein, for use in a method of treatment of atherosclerosis of the human or animal body by therapy.

Another aspect of the present invention pertains to compounds of Formula (I), as described herein, for use in a method of raising HDL of the human or animal body by therapy.

Another aspect of the present invention pertains to uses of the compounds of Formula (I), as described herein, for the manufacture of a medicament for use in the treatment of a metabolic-related disorder.

Another aspect of the present invention pertains to uses of the compounds of Formula (I), as described herein, for the manufacture of a medicament for use in the treatment of a metabolic-related disorder selected from the group consisting of dyslipidemia, atherosclerosis, coronary heart disease, insulin resistance, obesity, impaired glucose tolerance, atheromatous disease, hypertension, stroke, Syndrome X, heart disease and type 2 diabetes.

Another aspect of the present invention pertains to uses of the compounds of Formula (I), as described herein, for the manufacture of a medicament for use in the treatment of atherosclerosis.

Another aspect of the present invention pertains to uses of the compounds of Formula (I), as described herein, for the manufacture of a medicament for use in raising HDL in an individual.

Some embodiments of the present invention relate to methods of treatment of metabolic-related disorders. In some embodiments the metabolic-related disorder is of the group consisting of dyslipidemia, atherosclerosis, coronary heart disease, insulin resistance, obesity, impaired glucose tolerance, atheromatous disease, hypertension, stroke, Syndrome X, heart disease and type 2 diabetes. In some embodiments the metabolic-related disorder is dyslipidemia, atherosclerosis, coronary heart disease, insulin resistance and type 2 diabetes. In some embodiments the metabolic-related disorder is dyslipidemia. In some embodiments the metabolic-related disorder is atherosclerosis. In some embodiments the metabolic-related disorder is coronary heart disease. In some embodiments the metabolic-related disorder is insulin resistance. In some embodiments the metabolic-related disorder is type 2 diabetes.

In some embodiments related to methods of the present invention, the individual is a mammal. In further embodiments, the mammal is a human.

Another aspect of the present invention pertains to methods of producing a pharmaceutical composition comprising admixing or combining a compound of Formula (I), as described herein and a pharmaceutically acceptable carrier.

Compositions of the Present Invention

Some embodiments of the present invention include pharmaceutical compositions comprising a compound according to Formula (I) in combination with a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations can be prepared by any suitable method, typically by uniformly mixing the active compound(s) with liquids or finely divided solid carriers or both, in the required proportions and then, if necessary, forming the resulting mixture into a desired shape.

Conventional excipients, such as binding agents, fillers, acceptable wetting agents, tabletting lubricants and disintegrants can be used in tablets and capsules for oral administration. Liquid preparations for oral administration can be in the form of solutions, emulsions, aqueous or oily suspensions and syrups. Alternatively, the oral preparations can be in the form of dry powder that can be reconstituted with water or another suitable liquid vehicle before use. Additional additives such as suspending or emulsifying agents, non-aqueous vehicles (including edible oils), preservatives and flavorings and colorants can be added to the liquid preparations. Parenteral dosage forms can be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, The Science and Practice of Pharmacy, 20$^{th}$ Edition, 2000, Lippincott Williams & Wilkins, (Editors: Gennaro, A. R., et al.).

While it is possible that a compound for use in the treatment of the present invention may, in an alternative use, be administered as a raw or pure chemical, it is preferable however to present the compound or "active ingredient" as a pharmaceutical formulation or composition further comprising a pharmaceutically acceptable carrier. Therefore, one aspect of the present invention encompasses pharmaceutical compositions comprising a pharmaceutically acceptable carrier in combination with at least one compound according to Formula (I).

The invention provides pharmaceutical formulations comprising a compound of the invention or a pharmaceutically acceptable salt, hydrate or solvate thereof together with one or more pharmaceutically acceptable carriers therefor. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier or diluent, may thus be placed into the form of pharmaceutical formulations and unit dosages thereof and in such form can be employed as solids, such as tablets or filled capsules or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition can be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water can be used as a suitable pharmaceutically acceptable carrier.

Compounds of the present invention or a solvate or physiologically functional derivative thereof can be used as active ingredients in pharmaceutical compositions, specifically as RUP25 receptor agonists. By the term "active ingredient" is defined in the context of a "pharmaceutical composition" and shall mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits and as is customary and is known to the physician, it is to be tailored to the individual conditions in each individual case. It depends, for example, on the nature and severity of the illness to be treated, on the condition of the patient, on the compound employed or on whether an acute or chronic disease state is treated is conducted or on whether further active compounds are administered in addition to the compounds of the present invention. Representative doses of the present invention include, but not limited to, about 0.001 mg to about 5000 mg, about 0.001 to about 2500 mg, about 0.001 to about 1000 mg, 0.001 to about 500 mg, 0.001 mg to about 250 mg, about 0.001 mg to 100 mg, about 0.001 mg to about 50 mg and about 0.001 mg to about 25 mg. Multiple doses can be administered during the day, especially when relatively large amounts are deemed to be needed, for example 2, 3 or 4, doses. Depending on the individual and as deemed appropriate from the patient's physician or care-giver it may be necessary to deviate upward or downward from the doses described herein.

The amount of active ingredient or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system to another, for example, an animal model to a human. Typically, animal models include, but are not limited to, the rodents diabetes models as described in Example 1, infra; the mouse artherosclerosis model as described in Example 2, infra; or the in vivo animal arthosclerosis model as described in Example 5, infra. In some circumstances, these extrapolations may merely be based on the weight of the animal model in comparison to another, such as a mammal, preferably a human, however, more often, these extrapolations are not simply based on weight differences, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated is conducted or on whether further active compounds are administered in addition to the compounds of the Formula (I) and as part of a drug combination. The dosage regimen for treating a disease condition with the compounds and/or compositions of this invention is selected in accordance with a variety factors, such as, those cited above. Thus, the actual dosage regimen employed may vary widely and therefore may deviate from a preferred dosage regimen and one skilled in the art will recognize that dosage and dosage regimen outside these typical ranges can be tested and, where appropriate, can be used in the methods of this invention.

The desired dose may conveniently be presented in a single dose or as divided doses administered at appropriate intervals, for example, as two, three, four or more sub-doses per day. The sub-dose itself can be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it can be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories and dispersible granules. A solid carrier can be one or more substances which may also act as diluents, flavouring agents, solubilizers, lubricants, suspending agents, binders, preservatives, tablet disintegrating agents or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration can be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and can be presented in unit dose form in ampoules, pre-filled syringes, small volume infusion or in multi-dose containers with an added preservative. The compositions may take such forms as suspensions, solutions or emulsions in oily or aqueous vehicles and may contain formulatory agents such as suspending, stabilizing and/or dispersing agents. Alternatively, the active ingredient can be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose or other well known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents, and the like.

For topical administration to the epidermis the compounds according to the invention can be formulated as ointments, creams or lotions or as a transdermal patch.

Ointments and creams may, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations can be provided in single or multi-dose form. In the latter case of a dropper or pipette, this can be achieved by the patient administering an appropriate, predetermined volume of the solution or suspension. In the case of a spray, this can be achieved for example by means of a metering atomizing spray pump.

Administration to the respiratory tract may also be achieved by means of an aerosol formulation in which the active ingredient is provided in a pressurized pack with a suitable propellant. If the compounds of the Formula (I) or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the Formula (I) as an aerosol can be prepared by processes well-known to the person skilled in the art. For their preparation, for example, solutions or dispersions of the compounds of the Formula (I) in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFC's, such as, dichlorodifluoromethane, trichlorofluoromethane or dichlorotetrafluoroethane, and the like. The aerosol may conveniently also contain a surfactant such as lecithin. The dose of drug can be controlled by provision of a metered valve.

In formulations intended for administration to the respiratory tract, including intranasal formulations, the compound will generally have a small particle size for example of the order of 10 microns or less. Such a particle size can be obtained by means known in the art, for example by micronization. When desired, formulations adapted to give sustained release of the active ingredient can be employed.

Alternatively the active ingredients can be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition can be presented in unit dose form for example in capsules or cartridges of, e.g., gelatin or blister packs from which the powder can be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet or lozenge itself or it can be the appropriate number of any of these in packaged form.

Tablets or capsules for oral administration and liquids for intravenous administration are preferred compositions.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In general, the "pro-drug" approach is utilized to facilitate oral absorption. A thorough discussion is provided in T. Higuchi and V. Stella, "Pro-drugs as Novel Delivery Systems," Vol. 14 of the A.C.S. Symposium Series and in Bioreversible Carriers in Drug Design, ed. Edward B. Roche, American Pharmaceutical Association and Pergamon Press, 1987, both of which are hereby incorporated by reference in their entirety.

Combination Therapy:

While the compounds of the present invention can be administered as the sole active pharmaceutical agent (i.e., mono-therapy), they can also be used in combination with other pharmaceutical agents (i.e., combination-therapy) for the treatment of the diseases/conditions/disorders described herein. Therefore, another aspect of the present invention includes methods of treatment of metabolic related diseases comprising administering to an individual in need of such treatment a therapeutically-effective amount of a compound of the present invention in combination with one or more additional pharmaceutical agent as described herein.

Suitable pharmaceutical agents that can be used in combination with the compounds of the present invention include anti-obesity agents such as apolipoprotein-B secretion/microsomal triglyceride transfer protein (apo-B/MTP) inhibitors, MCR-4 agonists, cholecystokinin-A (CCK-A) agonists, serotonin and norepinephrine reuptake inhibitors (for example, sibutramine), sympathomimetic agents, $\beta_3$ adrenergic receptor agonists, dopamine agonists (for example, bromocriptine), melanocyte-stimulating hormone receptor analogs, cannabinoid 1 receptor antagonists [for example, SR141716: N-(piperidin-1-yl)-5-(4-chlorophenyl)-1-(2,4- dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e. orlistat), anorectic agents (such as a bombesin agonist), Neuropeptide-Y antagonists, thyromimetic agents, dehydroepiandrosterone or an analogue thereof, glucocorticoid receptor agonists or antagonists orexin receptor antagonists, urocortin binding protein antagonists, glucagon-like peptide-1 receptor agonists, ciliary neutrotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or reverse agonists, neuromedin U receptor agonists, noradrenergic anorectic agents (for example, phentermine, mazindol, and the like) and appetite suppressants (for example, bupropion).

Other anti-obesity agents, including the agents set forth infra, are well known or will be readily apparent in light of the instant disclosure, to one of ordinary skill in the art.

In some embodiments, the anti-obesity agents are selected from the group consisting of orlistat, sibutramine, bromocriptine, ephedrine, leptin and pseudoephedrine. In a further embodiment, compounds of the present invention and combination therapies are administered in conjunction with exercise and/or a sensible diet.

It is understood that the scope of combination-therapy of the compounds of the present invention with other anti-obesity agents, anorectic agents, appetite suppressant and related agents is not limited to those listed above, but includes in principle any combination with any pharmaceutical agent or pharmaceutical composition useful for the treatment of overweight and obese individuals.

Other suitable pharmaceutical agents, in addition to anti-obesity agents, that can be used in combination with the compounds of the present invention include agents useful in the treatment of concomitant disorders. Treatment of such disorders include the use of one or more pharmaceutical agents known in the art that belong to the classes of drugs referred to, but not limited to, the following: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate, and the like; bile acid sequestrants which include: cholestyramine, colestipol, and the like; and niacin), antiplatelet agents (for example, aspirin and adenosine diphosphate receptor antagonists that include: clopidogrel, ticlopidine, and the like), angiotensin-converting enzyme inhibitors, angiotensin II receptor antagonists and adiponectin. In accordance to one aspect of the present invention, a compound of the present can be used in combination with a pharmaceutical agent or agents belonging to one or more of the classes of drugs cited herein.

It is understood that the scope of combination-therapy of the compounds of the present invention with other pharmaceutical agents is not limited to those listed herein, supra or infra, but includes in principle any combination with any pharmaceutical agent or pharmaceutical composition useful for the treatment of diseases, conditions or disorders that are linked to metabolic-related disorders.

Some embodiments of the present invention include methods of treatment of a disease, disorder or condition as described herein comprising administering to an individual in need of such treatment a therapeutically effect amount or dose of a compound of the present invention in combination with at least one pharmaceutical agent selected from the group consisting of: sulfonylureas, meglitinides, biguanides, α-glucosidase inhibitors, peroxisome proliferators-activated receptors (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate, and the like; bile acid sequestrants which include: cholestyramine, colestipol, and the like; and niacin), antiplatelet agents (for example, aspirin and adenosine diphosphate receptor antagonists that include: clopidogrel, ticlopidine, and the like), angiotensin-converting enzyme inhibitors, angiotensin II receptor antagonists and adiponectin. In some embodiments, the pharmaceutical composition further comprises one or more agents selected from the group consisting of α-glucosidase inhibitor, aldose reductase inhibitor, biguanide, HMG-CoA reductase inhibitor, squalene synthesis inhibitor, fibrate, LDL catabolism enhancer, angiotensin converting enzyme inhibitor, insulin secretion enhancer and thiazolidinedione.

One aspect of the present invention encompasses pharmaceutical compositions comprising at least one compound according to Formula (I), as described herein. In some embodiments, the pharmaceutical composition further comprises one or more agents selected from the group consisting of, for example, α-glucosidase inhibitor, aldose reductase inhibitor, biguanide, HMG-CoA reductase inhibitor, squalene synthesis inhibitor, fibrate, LDL catabolism enhancer, angiotensin converting enzyme inhibitor, insulin secretion enhancer and thiazolidinedione.

Suitable pharmaceutical agents that can be used in conjunction with compounds of the present invention include α-glucosidase inhibitors. α-Glucosidase inhibitors belong to the class of drugs which competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Some representative examples of α-glucosidase inhibitors include acarbose, N-(1,3-dihydroxy-2-propyl)valiolanine (generic name; voglibose), miglitol and α-glucosidase inhibitors known in the art.

Suitable pharmaceutical agents that can be used in conjunction with compounds of the present invention include sulfonylureas. The sulfonylureas (SU) are drugs which promote secretion of insulin from pancreatic β cells by transmitting signals of insulin secretion via SU receptors in the cell membranes. Examples of the sulfonylureas include glyburide, glipizide, glimepiride and other sulfonylureas known in the art.

Suitable pharmaceutical agents that can be used in conjunction with compounds of the present invention include the meglitinides. The meglitinides are benzoic acid derivatives represent a novel class of insulin secretagogues. These agents target postprandial hyperglycemia and show comparable efficacy to sulfonylureas in reducing $HbA_{1c}$. Examples of meglitinides include repaglinide, nateglinide and other meglitinides known in the art.

Suitable pharmaceutical agents that can be used in conjunction with compounds of the present invention include the biguanides. The biguanides represent a class of drugs that stimulate anaerobic glycolysis, increase the sensitivity to insulin in the peripheral tissues, inhibit glucose absorption from the intestine, suppress of hepatic gluconeogenesis and inhibit fatty acid oxidation. Examples of biguanides include phenformin, metformin, buformin and biguanides known in the art.

Suitable pharmaceutical agents that can be used in conjunction with compounds of the present invention include the α-glucosidase inhibitors. The α-glucosidase inhibitors competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Examples of α-glucosidase inhibitors include acarbose, N-(1,3-dihydroxy-2-propyl)valiolamine (generic name; voglibose), miglitol and α-glucosidase inhibitors known in the art.

Suitable pharmaceutical agents that can be used in conjunction with compounds of the present invention include the peroxisome proliferators-activated receptor-γ (i.e., PPAR-γ) agonists. The peroxisome proliferators-activated receptor-γ agonists represent a class of compounds that activates the nuclear receptor PPAR-γ and therefore regulate the transcription of insulin-responsive genes involved in the control of glucose production, transport and utilization. Agents in the class also facilitate the regulation of fatty acid metabolism. Examples of PPAR-γ agonists include rosiglitazone, pioglitazone, tesaglitazar, netoglitazone, GW-409544, GW-501516 and PPAR-γ agonists known in the art.

Suitable pharmaceutical agents that can be used in conjunction with compounds of the present invention include the HMG-CoA reductase inhibitors. The HMG-CoA reductase inhibitors are agents also referred to as Statin compounds that belong to a class of drugs that lower blood cholesterol levels by inhibiting hydroxymethylglutalkyl CoA (HMG-CoA) reductase. HMG-CoA reductase is the rate-limiting enzyme in cholesterol biosynthesis. The statins lower serum LDL concentrations by upregulating the activity of LDL receptors and are responsible for clearing LDL from the blood. Some representative examples the statin compounds include rosuvastatin, pravastatin and its sodium salt, simvastatin, lovastatin, atorvastatin, fluvastatin, cerivastatin, rosuvastatin, pitavastatin, BMS's "superstatin" and HMG-CoA reductase inhibitors known in the art.

Suitable pharmaceutical agents that can be used in conjunction with compounds of the present invention include the angiotensin converting enzyme (ACE) inhibitors. The angiotensin converting enzyme inhibitors belong to the class of drugs that partially lower blood glucose levels as well as lowering blood pressure by inhibiting angiotensin converting enzymes. Examples of the angiotensin converting enzyme inhibitors include captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril and angiotensin converting enzyme inhibitors known in the art.

Suitable pharmaceutical agents that can be used in conjunction with compounds of the present invention include the angiotensin II receptor antagonists. Angiotensin II receptor antagonists target the angiotensin II receptor subtype 1 (i.e., AT1) and demonstrate a beneficial effect on hypertension. Examples of angiotensin II receptor antagonists include losartan (and the potassium salt form) and angiotensin II receptor antagonists known in the art.

Other treatments for one or more of the diseases cited herein include the use of one or more pharmaceutical agents known in the art that belong to the classes of drugs referred to, but not limited to, the following: amylin agonists (for example, pramlintide), insulin secretagogues (for example, GLP-1 agonists; exendin-4; insulinotropin (NN2211); dipeptyl-peptidase inhibitors (for example, NVP-DPP-728), acyl CoA cholesterol acetyltransferase inhibitors (for example, Ezetimibe, eflucimibe and like compounds), cholesterol absorption inhibitors (for example, ezetimibe, pamaqueside and like compounds), cholesterol ester transfer protein inhibitors (for example, CP-529414, JTT-705, CETi-1 and like compounds), microsomal triglyceride transfer protein inhibitors (for example, implitapide and like compounds), cholesterol modulators (for example, NO-1886 and like compounds), bile acid modulators (for example, GT103-279 and like compounds) and squalene synthase inhibitors.

Squalene synthesis inhibitors belong to a class of drugs that lower blood cholesterol levels by inhibiting synthesis of squalene. Examples of the squalene synthesis inhibitors include (S)-α-[Bis[2,2-dimethyl-1-oxopropoxy)methoxy] phosphinyl]-3-phenoxybenzenebutanesulfonic acid, mono potassium salt (BMS-188494) and squalene synthesis inhibitors known in the art.

In accordance with the present invention, the combination of a compound of the present invention and pharmaceutical agent can be prepared by mixing the respective active components either all together or independently with a pharmaceutically acceptable carrier, excipient, binder, diluent, etc. as described herein, and administering the mixture or mixtures either orally or non-orally as a pharmaceutical composition. When a compound or a mixture of compounds of Formula (I) are administered as a combination therapy with another active compound the therapeutic agents can be formulated as a separate pharmaceutical compositions given at the same time or at different times or the therapeutic agents can be given as a single composition.

Labeled Compounds and Assay Methods

Another object of the present invention relates to radio-labeled compounds of Formula (I) that are useful not only in radio-imaging but also in assays, both in vitro and in vivo, for localizing and quantitating RUP25 in tissue samples, including human and for identifying RUP25 ligands by inhibition binding of a radio-labeled compound. It is a further object of this invention to include novel RUP25 assays of which comprise such radio-labeled compounds.

The present invention embraces isotopically-labeled compounds of Formula (I) and any subgenera herein, such as but not limited to, Formulae (Ia) to (Ik). An "isotopically" or "radio-labeled" compounds are those which are identical to compounds disclosed herein, but for the fact that one or more atoms are replaced or substituted by an atom having an atomic mass or mass number different from the atomic mass or mass number typically found in nature (i.e., naturally occurring). Suitable radionuclides that can be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro RUP25 labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound of Formula (I) that has incorporated at least one radionuclide; in some embodiments the radionuclide is selected from the group consisting of $^{3}H$, $^{14}C$, $^{125}I$, $^{35}S$ and $^{82}Br$.

Certain isotopically-labeled compounds of the present invention are useful in compound and/or substrate tissue distribution assays. In some embodiments the radionuclide $^{3}H$ and/or $^{14}C$ isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence can be preferred in some circumstances. Isotopically labeled compounds of the present invention can generally be prepared by following procedures analogous to those disclosed in the Schemes supra and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the more scarce radio-isotope or nonradio-active isotope.

Synthetic methods for incorporating radio-isotopes into organic compounds are applicable to compounds of the invention and are well known in the art. These synthetic methods, for example, incorporating activity levels of tritium into target molecules and are as follows:

A. Catalytic Reduction with Tritium Gas—This procedure normally yields high specific activity products and requires halogenated or unsaturated precursors.

B. Tritium Gas Exposure Labeling—This procedure involves exposing precursors containing exchangeable protons to tritium gas in the presence of a suitable catalyst.

C. N-Methylation using Methyl Iodide [$^3$H]—This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions—This procedure transforms an aryl or heteroaryl amine into a diazonium salt, such as a tetrafluoroborate salt and subsequently to $^{125}$I labeled compound using Na$^{125}$I. A represented procedure was reported by Zhu, D.-G. and co-workers in *J. Org. Chem.* 2002, 67, 943-948.

B. Ortho $^{125}$Iodination of phenols—This procedure allows for the incorporation of $^{125}$I at the ortho position of a phenol as reported by Collier, T. L. and co-workers in *J. Labeled Compd. Radiopharm.* 1999, 42, S264-S266.

C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D. and co-workers in *J. Labeled Compd Radiopharm.* 2001, 44, S280-S282.

A radio-labeled RUP25 compound of Formula (I) can be used in a screening assay to identify/evaluate compounds. In general terms, a newly synthesized or identified compound (i.e., test compound) can be evaluated for its ability to reduce binding of the "radio-labeled compound of Formula (I)" to the RUP25 receptor. Accordingly, the ability of a test compound to compete with the "radio-labeled compound of Formula (I)" for the binding to the RUP25 receptor directly correlates to its binding affinity.

The labeled compounds of the present invention bind to the RUP25 receptor. In one embodiment the labeled compound has an EC$_{50}$ less than about 500 µM, in another embodiment the labeled compound has an EC$_{50}$ less than about 100 µM, in yet another embodiment the labeled compound has an EC$_{50}$ less than about 10 µM, in yet another embodiment the labeled compound has an EC$_{50}$ less than about 1 µM and in still yet another embodiment the labeled inhibitor has an EC$_{50}$ less than about 0.1 µM.

Other uses of the disclosed receptors and methods will become apparent to those in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

The following Examples are provided for illustrative purposes and not as a means of limitation. One of ordinary skill in the art would be able to design equivalent assays and methods based on the disclosure herein, all of which form part of the present invention.

Example 1

Rodent Diabetes Models

Rodent models of type 2 diabetes associated with obesity and insulin resistance have been developed. Genetic models such as db/db and ob/ob [see Diabetes (1982) 31:1-6] in mice and fa/fa in zucker rats have been developed for understanding the pathophysiology of disease and for testing candidate therapeutic compounds [Diabetes (1983) 32:830-838; Annu Rep Sankyo Res Lab (1994) 46:1-57]. The homozygous animals, C57 BL/KsJ-db/db mice developed by Jackson Laboratory are obese, hyperglycemic, hyperinsulinemic and insulin resistant [J Clin Invest (1990) 85:962-967], whereas heterozygotes are lean and normoglycemic. In the db/db model, mice progressively develop insulinopenia with age, a feature commonly observed in late stages of human type 2 diabetes when sugar levels are insufficiently controlled. Since this model resembles that of human type 2 diabetes, the compounds of the present invention are tested for activities including, but not limited to, lowering of plasma glucose and triglycerides. Zucker (fa/fa) rats are severely obese, hyperinsulinemic and insulin resistant {Coleman, Diabetes (1982) 31:1; E Shafrir in Diabetes Mellitus, H Rifkin and D Porte, Jr, Eds [Elsevier Science Publishing Co, New York, ed. 4, (1990), pp. 299-340]} and the fa/fa mutation may be the rat equivalent of the murine db mutation [Friedman et al, Cell (1992) 69:217-220; Truett et al, Proc Natl Acad Sci USA (1991)88:7806]. Tubby (tub/tub) mice are characterized by obesity, moderate insulin resistance and hyperinsulinemia without significant hyperglycemia [Coleman et al, Heredity (1990) 81:424].

The present invention encompasses the use of compounds of the invention for reducing the insulin resistance and hyperglycemia in any or all of the above rodent diabetes models, in humans with type 2 diabetes or other preferred metabolic-related disorders or disorders of lipid metabolism described previously or in models based on other mammals. Plasma glucose and insulin levels will be tested, as well as other factors including, but not limited to, plasma free fatty acids and triglycerides.

In Vivo Assay for Anti-Hyperglycemic Activity of Compounds of the Invention

Genetically altered obese diabetic mice (db/db) (male, 7-9 weeks old) are housed (7-9 mice/cage) under standard laboratory conditions at 22° C. and 50% relative humidity and maintained on a diet of Purina rodent chow and water ad libitum. Prior to treatment, blood is collected from the tail vein of each animal and blood glucose concentrations are determined using One Touch Basic Glucose Monitor System (Lifescan). Mice that have plasma glucose levels between 250 to 500 mg/dl are used. Each treatment group consists of seven mice that are distributed so that the mean glucose levels are equivalent in each group at the start of the study. db/db mice are dosed by micro-osmotic pumps, inserted using isoflurane anesthesia, to provide compounds of the invention, saline or an irrelevant compound to the mice subcutaneously (s.c.). Blood is sampled from the tail vein at intervals thereafter and analyzed for blood glucose concentrations. Significant differences between groups (comparing compounds of the invention to saline-treated) are evaluated using Student t-test.

Example 2

Mouse Atherosclerosis Model

Adiponectin-deficient mice generated through knocking out the adiponectin gene have been shown to be predisposed to atherosclerosis and to be insulin resistant. The mice are also a suitable model for ischemic heart disease [Matsuda, M et al. J Biol Chem (2002) July and references cited therein, the disclosures of which are incorporated herein by reference in their entirety].

Adiponectin knockout mice are housed (7-9 mice/cage) under standard laboratory conditions at 22° C. and 50% relative humidity. The mice are dosed by micro-osmotic pumps, inserted using isoflurane anesthesia, to provide compounds of the invention, saline or an irrelevant compound to the mice subcutaneously (s.c.). Neointimal thickening and ischemic heart disease are determined for different groups of mice sacrificed at different time intervals. Significant differences between groups (comparing compounds of the invention to saline-treated) are evaluated using Student t-test.

Example 3

In Vitro Biological Activity

A modified Flash Plate™ Adenylyl Cyclase kit (New England Nuclear; Cat. No. SMP004A) was utilized for direct identification of candidate compounds as agonists to hRUP25 (Seq. Id. Nos. 1 & 2) in accordance with the following protocol:

CHO cells stably transfected with an expression vector encoding hRUP25 and cultured under condition permissive for cell surface expression of the encoded hRUP25 receptor were harvested from flasks via non-enzymatic means. The cells were washed in PBS and resuspended in the manufacturer's Assay Buffer. Live cells were counted using a hemacytometer and Trypan blue exclusion and the cell concentration was adjusted to $2 \times 10^6$ cells/ml. cAMP standards and Detection Buffer (comprising 2 µCi of tracer $[^{125}I]$-cAMP (100 µl) to 11 ml Detection Buffer) were prepared and maintained in accordance with the manufacturer's instructions. Candidate compounds identified as per above (if frozen, thawed at room temperature) were added to their respective wells (preferably wells of a 96-well plate) at increasing concentrations (3 µl/well; 12 µM final assay concentration). To these wells, 100,000 cells in 50 µl of Assay Buffer were added and the mixture was then incubated for 30 minutes at room temperature, with gentle shaking. Following the incubation, 100 µl of Detection Buffer was added to each well, followed by incubation for 2-24 hours. Plates were counted in a Wallac MicroBeta™ plate reader using "Prot. #31" (as per manufacturer instructions).

Example 4

Representative Biological Activity

The biological in vitro activity was determined using the cAMP Whole Cell method. Certain compounds of the invention have an $EC_{50}$ in the range of about 30 nM to about 20 µM.

Example 5

In Vivo Animal Model

One utility of the compound of the present invention as a medical agent in the prophylaxis and treatment of a high total cholesterol/HDL-cholesterol ratio and conditions relating thereto is demonstrated by the activity of the compound in lowering the ratio of total cholesterol to HDL-cholesterol, in elevating HDL-cholesterol or in protection from atherosclerosis in an in vivo pig model. Pigs are used as an animal model because they reflect human physiology, especially lipid metabolism, more closely than most other animal models. An illustrative in vivo pig model not intended to be limiting is presented here.

Yorkshire albino pigs (body weight 25.5±4 kg) are fed a saturated fatty acid rich and cholesterol rich (SFA-CHO) diet during 50 days (1 kg chow 35 kg$^{-1}$ pig weight), composed of standard chow supplemented with 2% cholesterol and 20% beef tallow [Royo T et al., *European Journal of Clinical Investigation* (2000) 30:843-52; which disclosure is hereby incorporated by reference in its entirety]. Saturated to unsaturated fatty acid ratio is modified from 0.6 in normal pig chow to 1.12 in the SFA-CHO diet. Animals are divided into two groups, one group (n=8) fed with the SFA-CHO diet and treated with placebo and one group (n=8) fed with the SFA-CHO diet and treated with the compound (3.0 mg kg$^{-1}$). Control animals are fed a standard chow for a period of 50 days. Blood samples are collected at baseline (2 days after the reception of the animals) and 50 days after the initiation of the diet. Blood lipids are analyzed. The animals are sacrificed and necropsied.

Alternatively, the foregoing analysis comprises a plurality of groups each treated with a different dose of the compound. Preferred doses are selected from the group consisting of: 0.1 mg kg$^{-1}$, 0.3 mg kg$^{-1}$, 1.0 mg kg$^{-1}$, 3.0 mg kg$^{-1}$, 10 mg kg$^{-1}$, 30 mg kg$^{-1}$ and 100 mg kg$^{-1}$. Alternatively, the foregoing analysis is carried out at a plurality of timepoints. Preferred timepoints are selected from the group consisting of 10 weeks, 20 weeks, 30 weeks, 40 weeks and 50 weeks.

HDL-Cholesterol

Blood is collected in trisodium citrate (3.8%, 1:10). Plasma is obtained after centrifugation (1200 g 15 min) and immediately processed. Total cholesterol, HDL-cholesterol and LDL-cholesterol are measured using the automatic analyzer Kodak Ektachem DT System (Eastman Kodak Company, Rochester, N.Y., USA). Samples with value parameters above the range are diluted with the solution supplied by the manufacturer and then re-analyzed. The total cholesterol/HDL-cholesterol ratio is determined. Comparison is made of the level of HDL-cholesterol between groups. Comparison is made of the total cholesterol/HDL-cholesterol ratio between groups.

Elevation of HDL-cholesterol or reduction of the total cholesterol/HDL-cholesterol ratio on administration of the compound is taken as indicative of the compound having the aforesaid utility.

Atherosclerosis

The thoracic and abdominal aortas are removed intact, opened longitudinally along the ventral surface and fixed in neutral-buffered formalin after excision of samples from standard sites in the thoracic and abdominal aorta for histological examination and lipid composition and synthesis studies. After fixation, the whole aortas are stained with Sudan IV and pinned out flat and digital images are obtained with a TV camera connected to a computerized image analysis system (Image Pro Plus; Media Cybernetics, Silver Spring, Md.) to determine the percentage of aortic surface involved with atherosclerotic lesions [Gerrity R G et al, *Diabetes* (2001) 50:1654-65; Cornhill J F et al, *Arteriosclerosis, Thrombosis and Vascular Biology* (1985) 5:415-26; which disclosures are hereby incorporated by reference in their entirety]. Comparison is made between groups of the percentage of aortic surface involved with atherosclerotic lesions.

Reduction of the percentage of aortic surface involved with atherosclerotic lesions on administration of the compound is taken as indicative of the compound having the aforesaid utility.

Example 6

Receptor Binding Assay

In addition to the methods described herein, another means for evaluating a test compound is by determining binding affinities to the RUP25 receptor. This type of assay generally requires a radiolabelled ligand to the RUP25 receptor. Absent the use of known ligands for the RUP25 receptor and radiolabels thereof, compounds of Formula (I) can be labelled with a radioisotope and used in an assay for evaluating the affinity of a test compound to the RUP25 receptor.

A radiolabelled RUP25 compound of Formula (I) can be used in a screening assay to identify/evaluate compounds. In general terms, a newly synthesized or identified compound (i.e., test compound) can be evaluated for its ability to reduce binding of the "radiolabelled compound of Formula (I)" to the RUP25 receptor. Accordingly, the ability to compete with the "radio-labelled compound of Formula (I)" or Radiolabelled RUP25 Ligand for the binding to the RUP25 receptor directly correlates to its binding affinity of the test compound to the RUP25 receptor.

Assay Protocol for Determining Receptor Binding for RUP25

A. RUP25 Receptor Preparation 293 cells (human kidney, ATCC), transiently transfected with 10 ug human RUP25 receptor and 60 ul Lipofectamine (per 15-cm dish), are grown in the dish for 24 hours (75% confluency) with a media change and removed with 10 ml/dish of Hepes-EDTA buffer (20 mM Hepes+10 mM EDTA, pH 7.4). The cells are centrifuged in a Beckman Coulter centrifuge for 20 minutes, 17,000 rpm (JA-25.50 rotor). Subsequently, the pellet is resuspended in 20 mM Hepes+1 mM EDTA, pH 7.4 and homogenized with a 50-ml Dounce homogenizer and again centrifuged. After removing the supernatant, the pellets are stored at −80° C., until used in binding assay. When used in the assay, membranes are thawed on ice for 20 minutes and then 10 mL of incubation buffer (20 mM Hepes, 1 mM $MgCl_2$, 100 mM NaCl, pH 7.4) added. The membranes are vortexed to resuspend the crude membrane pellet and homogenized with a Brinkmann PT-3100 Polytron homogenizer for 15 seconds at setting 6. The concentration of membrane protein is determined using the BRL Bradford protein assay.

B. Binding Assay

For total binding, a total volume of 50 ul of appropriately diluted membranes (diluted in assay buffer containing 50 mM Tris HCl (pH 7.4), 10 mM $MgCl_2$ and 1 mM EDTA; 5-50 ug protein) is added to 96-well polyproylene microtiter plates followed by addition of 100 ul of assay buffer and 50 ul of Radiolabelled RUP25 Ligand. For nonspecific binding, 50 ul of assay buffer is added instead of 100 ul and an additional 50 ul of 10 uM cold RUP25 is added before 50 ul of Radiolabelled RUP25 Ligand is added. Plates are then incubated at room temperature for 60-120 minutes. The binding reaction is terminated by filtering assay plates through a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plate are sealed, 50 ul of Optiphase Supermix is added to each well, the top of the plates are sealed and plates are counted in a Trilux MicroBeta scintillation counter. For compound competition studies, instead of adding 100 ul of assay buffer, 100 ul of appropriately diluted test compound is added to appropriate wells followed by addition of 50 ul of Radiolabelled RUP25 Ligand.

C. Calculations

The test compounds are initially assayed at 1 and 0.1 µM and then at a range of concentrations chosen such that the middle dose would cause about 50% inhibition of a Radio-RUP25 Ligand binding (i.e., $IC_{50}$). Specific binding in the absence of test compound ($B_O$) is the difference of total binding ($B_T$) minus non-specific binding (NSB) and similarly specific binding (in the presence of test compound) (B) is the difference of displacement binding ($B_D$) minus non-specific binding (NSB). $IC_{50}$ is determined from an inhibition response curve, logit-log plot of % $B/B_O$ vs concentration of test compound.

$K_i$ is calculated by the Cheng and Prustoff transformation:

$$K_i = IC_{50}/(1+[L]/K_D)$$

where [L] is the concentration of a Radio-RUP25 Ligand used in the assay and $K_D$ is the dissociation constant of a Radio-RUP25 Ligand determined independently under the same binding conditions.

Example 7

Flushing via Laser Doppler

Procedure—Male C57B16 mice (~25 g) are anesthetized using 10 mg/ml/kg Nembutal sodium. When antagonists are to be administered the are co-injected with the Nembutal anesthesia. After ten minutes the animal is placed under the laser and the ear is folded back to expose the ventral side. The laser is positioned in the center of the ear and focused to an intensity of 8.4-9.0 V (with is generally ~4.5 cm above the ear). Data acquisition is initiated with a 15 by 15 image format, auto interval, 60 images and a 20 sec time delay with a medium resolution. Test compounds are administered following the 10th image via injection into the peritoneal space. Images 1-10 are considered the animal's baseline and data is normalized to an average of the baseline mean intensities.

Materials and Methods—Laser Doppler Pirimed PimII; Niacin (Sigma); Nembutal (Abbott labs).

Example 8

Inhibition of Free Fatty-Acid Production, In Vivo, in Catheterized Male Sprague-Daly Rats FIG. 2A depicts nicotinic acid inhibiting plasma free fatty acid concentrations in food deprived animals at various concentrations.

FIG. 2B depicts Compound 1 is able to inhibit free fatty acid production to the same extent, at similar doses and within the same time-frame as compared to nicotinic acid dose-response.

Non-esterified free-fatty acid (NEFA) assays were done on serum derived from live, freely moving rats. Jugular vein catheters were surgically implanted into the jugular veins and the animals were allowed to recover at least 48 hr post surgery. Food was removed from the animals approximately 16 hours prior to the assay. A draw of ~200 μl blood was pulled from the catheter and represents the baseline NEFA serum sample. Drug was administered intra-peritoneally (IP) at various concentrations to individual rats and then ~200 μl blood draws were pulled from the catheter at the indicated time points for further NEFA analysis. NEFA assays were performed according to the manufacturer's specifications (Wako Chemicals, USA; NEFA C) and free fatty acid concentrations were determined via regression analysis of a known standard curve (range of known free fatty acids). Data was analyzed using Excel and PrismGraph.

Example 9

Compounds of the Invention—Syntheses

Example 9.1

5-Cyclohex-1-enyl-5-methyl-4-oxo-4,5-dihydro-furan-2-carboxylic acid (Compound 1)—General Synthesis

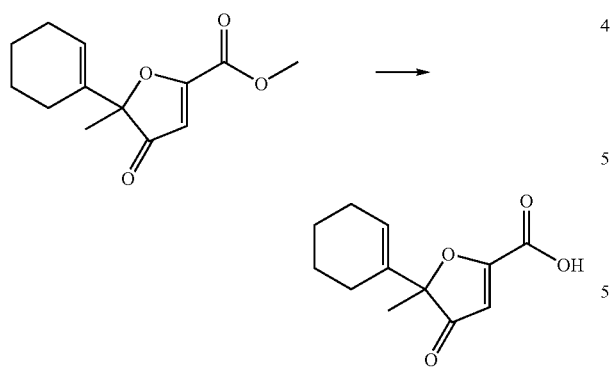

To a solution of 5-cyclohex-1-enyl-5-methyl-4-oxo-4,5-dihydro-furan-2-carboxylic acid methyl ester (47 mg, 0.2 mmol) in THF/MeOH (1/1, 2 mL) was added LiOH.H₂O (8.4 mg, 0.2 mmol). The reaction mixture was stirred at room temperature for 5 hours. After concentration, the residue was dissolved in H₂O (4 mL), washed with ethyl ether (2×5 mL). The separated aqueous layer was acidified to pH 2. This acidified solution was extracted with ethyl ether (3×5 mL). The extracts were dried (Na₂SO₄), filtered and concentrated. The crude product was purified with a silica gel column using EtOAc/AcOH (20/1) providing 35 mg (79%) of racemic 5-cyclohex-1-enyl-5-methyl-4-oxo-4,5-dihydro-furan-2-carboxylic acid: LC-MS m/z 221 (M−1); ¹H NMR (400 MHz, CDCl₃) δ 6.30 (s, 1H), 5.90 (m, 1H), 2.16-2.06 (m, 3H), 1.79-1.70 (m, 1H), 1.67-1.51 (m, 4H), 1.58 (s, 3H).

In intermediate 5-Cyclohex-1-enyl-5-methyl-4-oxo-4,5-dihydro-furan-2-carboxylic acid methyl ester was prepared in the following manner:

A. 1-Cyclohex-1-enyl-1-(2-methyl-[1,3]dithian-2-yl)-ethanol.

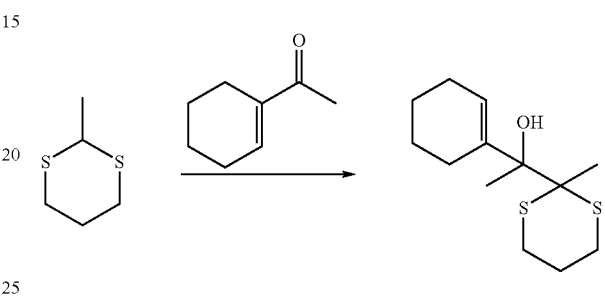

To an oven-dried round-bottom flask with stirring bar was added 2-methyl-[1,3]dithiane (4.31 mL, 36.0 mmol) and THF (150 mL). The flask was flushed with argon, cooled to −78° C. and n-butyl lithium (22.5 mL of 1.6 M solution in hexanes, 36.0 mmol) was added over 10 min. by syringe. The flask was warmed to −10° C., stirred for 2 h, cooled to −78° C. and 1-cyclohex-1-enyl-ethanone (3.73 g, 30.0 mmol) was added dropwise. After stirring overnight, the reaction was quenched with NH₄Cl (100 mL) and extracted with EtOAc (3×100 mL). The combined organic extracts were dried (Na₂SO₄), filtered and concentrated. The crude product was purified with a Biotage 60+M silica gel column using isocratic 9:1 Hexanes/EtOAc providing 5.17 g (67%) of 1-cyclohex-1-enyl-1-(2-methyl-[1,3]dithian-2-yl)-ethanol: ¹H NMR (400 MHz, CDCl₃) δ (m, 1H), 2.97-2.80 (m, 4H), 2.70 (bs, 1OH), 2.32-2.18 (m, 2H), 2.17-2.09 (m, 2H), 2.06-1.95 (m, 1H), 1.93-1.82 (m, 1H), 1.79 (s, 3H), 1.62-1.51 (m, 4H), 1.56 (s, 3H).

B. 3-Cyclohex-1-enyl-3-hydroxy-butan-2-one.

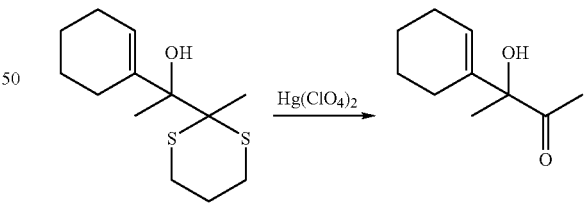

To a solution of 1-cyclohex-1-enyl-1-(2-methyl-[1,3]dithian-2-yl)-ethanol (5.17 g, 20.0 mmol) in MeOH (100 mL) was added Hg(ClO₄)₂ (16.0 g, 40.0 mmol). The suspension was stirred for 2 h at room temperature. The suspension was filtered through Celite and the filtrate was concentrated. The resulting residue was dissolved in H₂O (150 mL) and extracted with EtOAc (3×100 mL). The combined organic extracts were washed with H₂O (70 mL), dried (Na₂SO₄), filtered and concentrated. The crude product was purified on the SiO₂ column using a gradient of 2% to 41% EtOAc in hexanes providing 2.3 g (68%) of 3-cyclohex-1-enyl-3-hydroxy-butan-2-one: $^1$H NMR (400 MHz, CDCl$_3$) δ (m, 1H), 4.07 (s, 1OH), 2.14 (s, 3H), 2.14-2.09 (m, 2H), 1.68-1.48 (m, 6H), 1.46 (s, 3H).

C. 5-Cyclohex-1-enyl-5-methyl-4-oxo-4,5-dihydro-furan-2-carboxylic acid methyl ester.

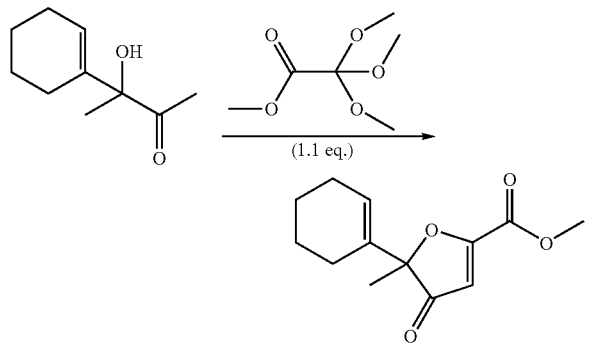

To an oven-dried 10 mL vial was added 3-cyclohex-1-enyl-3-hydroxy-butan-2-one (0.80 g, 4.80 mmol), THF (4 mL) and trimethoxy-acetic acid methyl ester (0.94 g, 5.76 mmol). The vial was capped with a septum and flushed with Ar. In a dried round-bottom flask with stirring bar was added sodium hydride (60% dispersion in mineral oil, 0.57 g, 14.4 mmol) and THF (20 mL). The flask was capped with a septum and flushed with Ar. The contents of the vial were added dropwise via syringe to the round-bottom flask. The round-bottom flask was equipped with a condenser and septum and heated to 65° C. under Ar for 12 h. The reaction was quenched with sat'd NH$_4$Cl (20 mL) and the layers were separated. The organic extract was concentrated and dissolved in 1,4-dioxane (4 mL). The solution was mixed with conc. HCl (0.5 mL) and stirred overnight at rt. Saturated NaHCO$_3$ solution (20 mL) was added and the reaction was extracted with EtOAc (3×50 mL). The extracts were dried (Na$_2$SO$_4$), filtered and concentrated. The crude product was purified with a Biotage 25+M silica gel column using a gradient of 0-10% EtOAc in hexanes providing 0.37 g (32%) of racemic 5-cyclohex-1-enyl-5-methyl-4-oxo-4,5-dihydro-furan-2-carboxylic acid methyl ester: LC-MS) m/z 235 (M−1); $^1$H NMR (400 MHz, CDCl$_3$) δ 6.20 (s, 1H), 5.90-5.88 (m, 1H), 3.96 (s, 3H), 2.14-2.04 (m, 3H), 1.87-1.78 (m, 1H), 1.63-1.52 (m, 4H), 1.54 (s, 3H).

Example 9.2

5-Methyl-4-oxo-5-thiophen-3-yl-4,5-dihydro-furan-2-carboxylic acid methyl ester (Compound 2)

5-Methyl-4-oxo-5-thiophen-3-yl-4,5-dihydro-furan-2-carboxylic acid methyl ester was prepared in a similar manner as described in Example 9.1. LC-MS m/z 239 (M+1); $^1$H NMR (400 MHz, DMSO-d$_6$) δ 7.64-7.61 (m, 2H), 7.13 (dd, J=4.9, 1.5 Hz, 1H), 6.46 (s, 1H), 3.94 (s, 3H), 1.76 (s, 3H).

Example 9.3

5-Methyl-4-oxo-5-thiophen-2-yl-4,5-dihydro-furan-2-carboxylic acid methyl ester (Compound 3)

5-Methyl-4-oxo-5-thiophen-2-yl-4,5-dihydro-furan-2-carboxylic acid methyl ester was prepared in a similar manner as described in Example 9.1. LC-MS m/z 239 (M+1); $^1$H NMR (400 MHz, CDCl$_3$) δ 7.30 (dd, J=5.1, 1.2 Hz, 1H), 7.10 (J=13.6, 1.1 Hz, 1H), 6.99 (dd, J=5.0, 3.6 Hz, 1H), 6.28 (s, 1H), 3.98 (s, 3H), 1.86 (s, 3H).

Example 9.4

5-(4-Bromo-thiophen-2-yl)-5-methyl-4-oxo-4,5-dihydro-furan-2-carboxylic acid methyl ester (Compound 4)

5-(4-Bromo-thiophen-2-yl)-5-methyl-4-oxo-4,5-dihydro-furan-2-carboxylic acid methyl ester was prepared in a similar manner as described in Example 9.1. LC-MS m/z 315 (M−1); $^1$H NMR (400 MHz, CDCl$_3$) δ 7.20 (d, J=1.4 Hz, 1H), 7.04 (d, J=1.4 Hz, 1H), 6.27 (s, 1H), 3.99 (s, 3H), 1.82 (s, 3H).

Example 9.5

5-(4-Bromo-thiophen-2-yl)-5-methyl-4-oxo-4,5-dihydro-furan-2-carboxylic acid (Compound 5)

5-(4-Bromo-thiophen-2-yl)-5-methyl-4-oxo-4,5-dihydro-furan-2-carboxylic acid was prepared in a similar manner as described in Example 9.1. LC-MS m/z 301 (M−1); $^1$H NMR (400 MHz, CDCl$_3$) δ 7.21 (d, J=1.4 Hz, 1H), 7.05 (d, J=1.4 Hz, 1H), 6.38 (s, 1H), 1.85 (s, 3H).

Example 9.6

5-Methyl-5-(5-methyl-thiophen-2-yl)-4-oxo-4,5-dihydro-furan-2-carboxylic acid methyl ester (Compound 6)

5-Methyl-5-(5-methyl-thiophen-2-yl)-4-oxo-4,5-dihydro-furan-2-carboxylic acid methyl ester was prepared in a similar manner as described in Example 9.1. LC-MS m/z 251 (M−1); $^1$H NMR (400 MHz, CDCl$_3$) δ 6.87 (d, J=3.6 Hz, 1H), 6.62 (dt, J=3.5, 1.0 Hz, 1H), 6.26 (s, 1H), 3.97 (s, 3H), 2.44 (s, 3H), 1.82 (s, 3H).

Example 9.7

5-Methyl-5-(5-methyl-thiophen-2-yl)-4-oxo-4,5-dihydro-furan-2-carboxylic acid (Compound 7)

5-Methyl-5-(5-methyl-thiophen-2-yl)-4-oxo-4,5-dihydro-furan-2-carboxylic acid was prepared in a similar manner as described in Example 9.1. LC-MS m/z 237 (M−1); $^1$H NMR (400 MHz, CDCl$_3$) δ 6.82 (d, J=2.8 Hz, 1H), 6.58 (bs, 1H), 6.26 (s, 1H), 2.41 (s, 3H), 1.80 (s, 3H).

Example 9.8

5-(5-Chloro-thiophen-2-3,1)-5-methyl-4-oxo-4,5-dihydro-furan-2-carboxylic acid methyl ester (Compound 8)

5-(5-Chloro-thiophen-2-yl)-5-methyl-4-oxo-4,5-dihydro-furan-2-carboxylic acid methyl ester was prepared in a similar manner as described in Example 9.1. LC-MS m/z 271 (M−1); $^1$H NMR (400 MHz, CDCl$_3$) δ 6.88 (d, J=3.9 Hz, 1H), 6.80 (d, J=3.9 Hz, 1H), 6.27 (s, 1H), 3.98 (s, 3H), 1.81 (s, 3H).

Example 9.9

5-Cyclopent-1-enyl-5-methyl-4-oxo-4,5-dihydro-furan-2-carboxylic acid (Compound 9)

5-Cyclopent-1-enyl-5-methyl-4-oxo-4,5-dihydro-furan-2-carboxylic acid was prepared in a similar manner as described in Example 9.1. LC-MS m/z 207 (M−1); $^1$H NMR (400 MHz, DMSO-$d_6$) δ 6.19 (s, 1H), 5.79 (m, 1H), 2.35-2.26 (m, 3H), 2.14-2.05 (m, 1H), 1.86-1.78 (m, 2H), 1.49 (s, 3H).

Example 9.10

5-Biphenyl-3-yl-5-methyl-4-oxo-4,5-dihydro-furan-2-carboxylic acid methyl ester (Compound 10)

5-Biphenyl-3-yl-5-methyl-4-oxo-4,5-dihydro-furan-2-carboxylic acid methyl ester was prepared in a similar manner as described in Example 9.1. $^1$H NMR (400 MHz, CDCl$_3$) δ 7.71 (t, J=1.8 Hz, 1H), 7.59-7.34 (m, 8H), 6.26 (s, 1H), 3.99 (s, 3H), 1.86 (s, 3H).

Example 9.11

5-Methyl-4-oxo-5-(3-thiophen-2-yl-phenyl)-4,5-dihydro-furan-2-carboxylic acid methyl ester (Compound 11)

5-Methyl-4-oxo-5-(3-thiophen-2-yl-phenyl)-4,5-dihydro-furan-2-carboxylic acid methyl ester was prepared in a similar manner as described in Example 9.1. $^1$H NMR (400 MHz; CDCl$_3$) δ 7.74(s, 1H), 7.56 (d, J=7.5 Hz, 1H), 7.44 (d, J=7.9 Hz, 1H), 7.37 (t, J=7.7 Hz, 1H), 7.33 (d, J=3.6 Hz, 1H), 7.30 (d, J=5.1 Hz, 1H), 7.08 (t, J=4.0 Hz, 1H), 6.26 (s, 1H), 4.01 (s, 3H), 1.84 (s, 3H).

Example 9.12

5-(3-Bromo-phenyl)-5-methyl-4-oxo-4,5-dihydro-furan-2-carboxylic acid methyl ester (Compound 12)

5-(3-Bromo-phenyl)-5-methyl-4-oxo-4,5-dihydro-furan-2-carboxylic acid methyl ester was prepared in a similar manner as described in Example 9.1. $^1$H NMR (400 MHz, CDCl$_3$) δ 7.65 (t, J=1.8 Hz, 1H), 7.46 (d, J=7.9 Hz, 1H), 7.45 (d, J=7.9 Hz, 1H), 7.24 (t, J=8.2 Hz, 1H), 6.24 (s, 1H), 4.00 (s, 3H), 1.78 (s, 3H).

Example 9.13

5-(3-Bromo-phenyl)-5-methyl-4-oxo-4,5-dihydro-furan-2-carboxylic acid (Compound 13)

5-(3-Bromo-phenyl)-5-methyl-4-oxo-4,5-dihydro-furan-2-carboxylic acid was prepared in a similar manner as described in Example 9.1. LC-MS m/z 295 (M−1); $^1$H NMR (400 MHz, CDCl$_3$) δ 7.66 (t, J=1.8 Hz, 1H), 7.49-7.45 (m, 2H), 7.25 (t, J=8.0 Hz, 1H), 6.36 (s, 1H), 1.81 (s, 3H).

Example 9.14

5-(3-Iodo-phenyl)-5-methyl-4-oxo-4,5-dihydro-furan-2-carboxylic acid (Compound 14)

5-(3-Iodo-phenyl)-5-methyl-4-oxo-4,5-dihydro-furan-2-carboxylic acid was prepared in a similar manner as described in Example 9.1. LC-MS m/z 343 (M−1); $^1$H NMR (400 MHz, CDCl$_3$) δ 7.84 (t, J=1.7 Hz, 1H), 7.68 (ddd, J=7.9, 1.6, 1.0 Hz, 1H), 7.51 (ddd, J=7.9, 1.7, 1.0 Hz, 1H), 7.11 (t, J=7.9 Hz, 1H), 6.36 (s, 1H), 1.80 (s, 3H).

Example 9.15

5-(3-Chloro-phenyl)-5-methyl-4-oxo-4,5-dihydro-furan-2-carboxylic acid (Compound 15)

5-(3-Chloro-phenyl)-5-methyl-4-oxo-4,5-dihydro-furan-2-carboxylic acid was prepared in a similar manner as described in Example 9.1. LC-MS m/z 251 (M−1); $^1$H NMR (400 MHz, CDCl$_3$) δ 7.42 (bs, 1H), 7.33 (bs, 1H), 7.25 (bs, 2H), 6.20 (s, 1H), 1.73 (s, 3H).

Example 9.16

5-(3-Fluoro-phenyl)-5-methyl-4-oxo-4,5-dihydro-furan-2-carboxylic acid (Compound 16)

5-(3-Fluoro-phenyl)-5-methyl-4-oxo-4,5-dihydro-furan-2-carboxylic acid was prepared in a similar manner as described in Example 9.1. $^1$H NMR (400 MHz, CD$_3$OD) δ 7.41 (td, J=8.0, 6.0 Hz, 1H), 7.33 (ddd, J=7.9, 1.5, 1.0 Hz, 1H), 7.24 (ddd, J=10.3, 2.4, 1.8 Hz, 1H), 7.08 (ddd, J=8.5, 2.5, 1.0 Hz, 1H), 6.22 (s, 1H), 1.77 (s, 3H).

Example 9.17

5-(3,5-Difluoro-phenyl)-5-methyl-4-oxo-4,5-dihydro-furan-2-carboxylic acid (Compound 17)

5-(3,5-Difluoro-phenyl)-5-methyl-4-oxo-4,5-dihydro-furan-2-carboxylic acid was prepared in a similar maimer as described in Example 9.1. LC-MS m/z 253 (M−1); $^1$H NMR (400 MHz, DMSO-$d_6$) δ 7.27 (tt, J=9.3, 2.3 Hz, 1H), 7.16-7.09 (m, 2H), 6.11 (s, 1H), 1.72 (s, 3H).

Example 9.18

5-Methyl-4-oxo-5-m-tolyl-4,5-dihydro-furan-2-carboxylic acid (Compound 18)

5-Methyl-4-oxo-5-m-tolyl-4,5-dihydro-furan-2-carboxylic acid was prepared in a similar manner as described in Example 9.1. $^1$H NMR (400 MHz, CDCl$_3$) δ 7.30 (d, J=7.3 Hz, 1H), 7.30 (s, 1H), 7.26 (t, J=7.3 Hz, 1H), 7.15 (d, J=7.3 Hz, 1H), 6.34 (s, 1H), 2.36 (s, 3H), 1.82 (s, 3H).

Example 9.19

5-(3-Ethyl-phenyl)-5-methyl-4-oxo-4,5-dihydro-furan-2-carboxylic acid (Compound 19)

5-(3-Ethyl-phenyl)-5-methyl-4-oxo-4,5-dihydro-furan-2-carboxylic acid was prepared in a similar manner as described in Example 9.1. LC-MS m/z 245 (M−1); $^1$H NMR (400 MHz, CDCl$_3$) δ 7.34-7.27 (m, 3H), 7.18 (d, J=7.1 Hz, 1H), 6.37 (s, 1H), 2.66 (q, J=8.0 Hz, 2H), 1.83 (s, 3H), 1.23 (t, J=8.0 Hz, 3H).

Example 9.20

5-Methyl-4-oxo-5-(3-trifluoromethyl-phenyl)-4,5-dihydro-furan-2-carboxylic acid (Compound 20)

5-Methyl-4-oxo-5-(3-trifluoromethyl-phenyl)-4,5-dihydro-furan-2-carboxylic acid was prepared in a similar manner as described in Example 9.1. ¹H NMR (400 MHz, CDCl₃) δ 7.78 (s, 1H), 7.74 (d, J=8.0 Hz, 1H), 7.60 (d, J=7.7 Hz, 1H), 7.51 (t, J=7.8 Hz, 1H), 6.34 (s, 1H), 1.83 (s, 3H).

Example 9.21

5-(5-Chloro-thiophen-2-yl)-5-methyl-4-oxo-4,5-dihydro-furan-2-carboxylic acid (Compound 21)

5-(5-Chloro-thiophen-2-yl)-5-methyl-4-oxo-4,5-dihydro-furan-2-carboxylic acid was prepared in a similar manner as described in Example 9.1. LC-MS m/z 257 (M−1); ¹H NMR (400 MHz, CDCl₃) δ 6.88 (d, J=3.9 Hz, 1H), 6.80 (d, J=3.9 Hz, 1H), 6.38 (s, 1H), 1.84 (s, 3H).

Example 9.22

5-Methyl-4-oxo-5-thiophen-2-yl-4,5-dihydro-furan-2-carboxylic acid (Compound 22)

5-Methyl-4-oxo-5-thiophen-2-yl-4,5-dihydro-furan-2-carboxylic acid was prepared in a similar manner as described in Example 9.1. LC-MS m/z 223 (M−1); ¹H NMR (400 MHz, CDCl₃) δ 7.31 (dd, J=5.1, 0.9 Hz, 1H), 7.11 (J=13.6, 0.9 Hz, 1H), 7.00 (dd, J=5.0, 3.7 Hz, 1H), 6.40 (s, 1H), 1.89 (s, 3H).

Example 9.23

5-(5-Bromo-thiophen-3-yl)-5-methyl-4-oxo-4,5-dihydro-furan-2-carboxylic acid methyl ester (Compound 23)

5-(5-Bromo-thiophen-3-yl)-5-methyl-4-oxo-4,5-dihydro-furan-2-carboxylic acid methyl ester was prepared in a similar manner as described in Example 9.1 except the intermediate 3-(5-bromo-thiophen-3-yl)-3-hydroxy-butan-2-one was prepared in a manner as described below. Compound 23 was characterized NMR and MS; LC-MS m/z 317 (M+1); ¹H NMR (400 MHz, CDCl₃) δ 7.25 (d, J=1.7 Hz, 1H), 7.12 (d, J=1.7 Hz, 1H), 6.25 (s, 1H), 3.99 (s, 3H), 1.75 (s, 3H).

The intermediate 3-(5-bromo-thiophen-3-yl)-3-hydroxy-butan-2-one was prepared using the following procedure.

A) 2-Bromo-4-(1-methyl-propenyl)-thiophene.

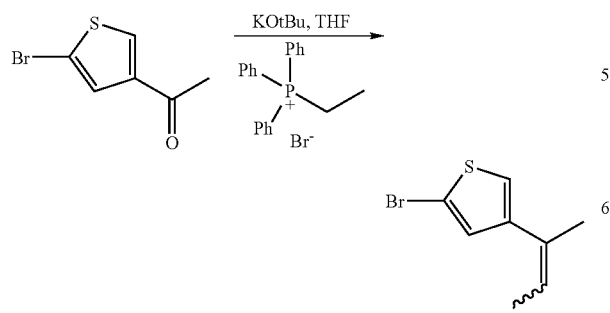

To a solution of ethyl-triphenyl-phosphonium bromide (27.0 mmol, 10.02 g) in anhydrous THF (90 mL) was added at 0° C. a solution of KOᵗBu (27.0 mmol, 27 mL, 1 M in THF). The solution was stirred for 1 h at room temperature, cooled down to −78° C. and treated with a solution of 1-(5-bromo-thiophen-3-yl)-ethanone (19.1 mmol, 3.92 g) in anhydrous THF (30 mL) at the temperature. The reaction mixture was slowly warmed to room temperature overnight with stirring. After dilution of the reaction mixture with EtOAc (200 mL), it was washed with water (70 mL×2) and brine (70 mL), dried (MgSO₄) and concentrated in vacuo. Chromatography on SiO₂ (Hexanes/EtOAc, 20/1) gave 4.15 g (100%) of 2-bromo-4-(1-methyl-propenyl)-thiophene as a liquid of isomeric mixture (Z/E isomer, 9/1). Z isomer; ¹H NMR (400 MHz, CDCl₃) δ 7.04 (d, J=1.7 Hz, 1H), 6.98 (d, J=1.7 Hz, 1H), 5.55 (m, 1H), 1.97 (quint, J=1.5 Hz, 3H), 1.72 (dq, J=7.0, 1.5 Hz, 3H). E isomer; ¹H NMR (400 MHz, CDCl₃) δ 7.17 (d, J=1.7 Hz, 1H), 6.94 (d, J=1.7 Hz, 1H), 5.90 (m, 1H), 1.94 (quint, J=1.1 Hz, 3H), 1.77 (d, J=6.9, 1.0 Hz, 3H).

B) 2-(5-Bromo-thiophen-3-yl)-butane-2,3-diol.

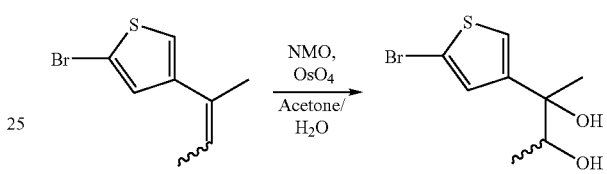

To a solution of 2-bromo-4-(1-methyl-propenyl)-thiophene (19.1 mmol, 4.15 g) in a cosolvent of acetone and water (15 mL/30 mL) was added at room temperature N-methyl morpholine oxide (NMO) (21.0 mmol, 4.92 g, 50% in H₂O) and OsO₄ (0.2 mmol, 1.27 g, 4% in H₂O). The reaction mixture was stirred for 24 h at the temperature. After evaporation of acetone in vacuo, it was extracted with EtOAc (70 mL×4). The combined solution was washed with brine (70 mL), dried (MgSO₄) and concentrated in vacuo. Chromatography on SiO₂ (EtOAc/Hexanes, 2/3) gave 4.3 g (90%) of 2-(5-bromo-thiophen-3-yl)-butane-2,3-diol as an oil of isomeric mixture (major/minor, 8/1). Major isomer; ¹H NMR (400 MHz, CDCl₃) δ 7.10 (d, J=1.7 Hz, 1H), 7.02 (d, J=1.7 Hz, 1H), 3.81 (m, 1H), 2.54 (s, 1OH), 1.99 (d, J=5.7 Hz, 1OH), 1.53 (s, 3H), 1.04 (d, J=6.4 Hz, 3H). Minor isomer; ¹H NMR (400 MHz, CDCl₃) δ 7.14 (d, J=1.7 Hz, 1H), 7.04 (d, J=1.7 Hz, 1H), 3.90 (m, 1H), 2.58 (s, 1OH), 2.07 (d, J=4.0 Hz, 1OH), 1.46 (s, 3H), 1.13 (d, J=6.4 Hz, 3H).

C) 3-(5-Bromo-thiophen-3-yl)-3-hydroxy-butan-2-one.

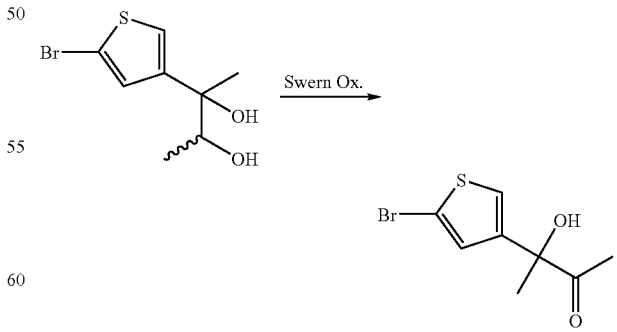

A solution of oxalyl chloride (19.12 mmol, 2.43 g) in anhydrous CH₂Cl₂ (100 mL) was cooled to −50° C. to −60° C. DMSO (39.83 mmol, 2.83 mL) is added dropwise at a rapid rate, with stirring. After 5 min, a solution of 2-(5- bromo-thiophen-3-yl)-butane-2,3-diol (15.93 mmol, 4.0 g) in anhydrous $CH_2Cl_2$ (25 mL) was added dropwise over 10 min, keeping the temperature at −50° C. to −60° C. After 15 min stirring, triethylamine (80 mmol, 11.15 mL) was added dropwise, keeping the temperature below −50° C. Stirring was then continued for 5 min. The reaction mixture was allowed to warm to room temperature and water (100 mL) was added. The separated aqueous layer was extracted with $CH_2Cl_2$ (70 mL×2). The combined organic layer was washed with brine (100 mL), dried ($MgSO_4$), concentrated in vacuo. Chromatography on $SiO_2$ (EtOAc/Hexanes, 1/2) gave 3.2 g (81%) of 3-(5-bromo-thiophen-3-yl)-3-hydroxy-butan-2-one as an oil; $^1$H NMR (400 MHz, $CDCl_3$) δ 7.22 (d, J=1.7 Hz, 1H), 6.98 (d, J=1.7 Hz, 1H), 4.48)s, 1OH), 2.16 (s, 3H), 1.72 (s, 3H).

Example 9.24

5-(5-Bromo-thiophen-3-yl)-5-methyl-4-oxo-4,5-dihydro-furan-2-carboxylic acid (Compound 24)

5-(5-Bromo-thiophen-3-yl)-5-methyl-4-oxo-4,5-dihydro-furan-2-carboxylic acid was prepared in a similar manner as described in Example 9.1. LC-MS m/z 301 (M−1); $^1$H NMR (400 MHz, DMSO-$d_6$) δ 7.56 (d, J=1.7 Hz, 1H), 7.23 (d, J=1.7 Hz, 1H), 6.30 (s, 1H), 1.69 (s, 3H).

Example 9.25

5-(5-Chloro-thiophen-3-yl)-5-methyl-4-oxo-4,5-dihydro-furan-2-carboxylic acid methyl ester (Compound 25)

5-(5-Chloro-thiophen-3-yl)-5-methyl-4-oxo-4,5-dihydro-furan-2-carboxylic acid methyl ester was prepared in a similar manner as described in Example 9.1. LC-MS m/z 273 M+1); $^1$H NMR (400 MHz, DMSO-$d_6$) δ 7.47 (d, J=1.7 Hz, 1H), 7.18 (d, J=1.7 Hz, 1H), 6.42 (s, 1H), 3.89 (s, 3), 1.70 (s, 3H).

Example 9.26

5-(5-Chloro-thiophen-3-yl)-5-methyl-4-oxo-4,5-dihydro-furan-2-carboxylic acid (Compound 26)

5-(5-Chloro-thiophen-3-yl)-5-methyl-4-oxo-4,5-dihydro-furan-2-carboxylic acid was prepared in similar maimer as described in Example 9.1. LC-MS m/z 259 (M+1); $^1$H NMR (400 MHz, DMSO-$d_6$) δ 7.45 (d, J=1.8 Hz, 1H), 7.15 (d, J=1.8 Hz, 1H), 6.30 (s, 1H), 1.68 (s, 3H).

Example 9.27

5-(4-Bromo-5-methyl-thiophen-2-yl)-5-methyl-4-oxo-4,5-dihydro-furan-2-carboxylic acid (Compound 27)

5-(4-Bromo-5-methyl-thiophen-2-yl)-5-methyl-4-oxo-4,5-dihydro-furan-2-carboxylic acid was prepared in a similar manner as described in Example 9.1. LC-MS m/z 315 (M−1); $^1$H NMR (400 MHz, $CDCl_3$) δ 6.92 (s, 1H), 6.38 (s, 1H), 2.36 (s, 3H), 1.82 (s, 3H).

Example 9.28

5-Methyl-4-oxo-5-thiophen-3-yl-4,5-dihydro-furan-2-carboxylic acid (Compound 28)

5-Methyl-4-oxo-5-thiophen-3-yl-4,5-dihydro-furan-2-carboxylic acid was prepared in a similar manner as described in Example 9.1. LC-MS m/z 223 (M−1); $^1$H NMR (400 MHz, $CDCl_3$) δ 7.37 (dd, J=2.9, 1.3 Hz, 1H), 7.34 (dd, J=5.0, 3.0 Hz, 1H), 7.17 (dd, J=5.0, 1.3 Hz, 1H), 6.39 (s, 1H), 1.82 (s, 3H).

Example 9.29

Preparation of Compounds of the Invention (Compounds 29 to 57)

Compounds 29 to 57 of the present invention were prepared in a similar manner as described herein. The MS data for each of these compounds are shown in the following table:

| Cmpd# | Chemical Name | m/z |
|---|---|---|
| 29 | 5-(4-Fluoro-phenyl)-5-methyl-4-oxo-4,5-dihydro-furan-2-carboxylic acid | 235.0 (M − 1) |
| 30 | 5-Methyl-4-oxo-5-pyridin-3-yl-4,5-dihydro-furan-2-carboxylic acid | 220.0 (M + 1) |
| 31 | 5-Ethyl-4-oxo-5-phenyl-4,5-dihydro-furan-2-carboxylic acid | 231.0 (M − 1) |
| 32 | 5-(2-Fluoro-phenyl)-5-methyl-4-oxo-4,5-dihydro-furan-2-carboxylic acid | 235.0 (M − 1) |
| 33 | 2-Methyl-3-oxo-2,3-dihydro-[2,2']bifuranyl-5-carboxylic acid | 207.0 (M − 1) |
| 34 | 5-(3,4-Difluoro-phenyl)-5-methyl-4-oxo-4,5-dihydro-furan-2-carboxylic acid | 253.2 (M − 1) |
| 35 | 5-(2,4-Difluoro-phenyl)-5-methyl-4-oxo-4,5-dihydro-furan-2-carboxylic acid | 253.2 (M − 1) |
| 36 | 5-(2,6-Difluoro-phenyl)-5-methyl-4-oxo-4,5-dihydro-furan-2-carboxylic acid | 253.2 (M − 1) |
| 37 | 5-(2,5-Dichloro-phenyl)-5-methyl-4-oxo-4,5-dihydro-furan-2-carboxylic acid | 285.2 (M − 1) |
| 38 | 5-(3-Methoxy-phenyl)-5-methyl-4-oxo-4,5-dihydro-furan-2-carboxylic acid | 247.0 (M − 1) |
| 39 | 5-Methyl-4-oxo-5-m-tolyl-4,5-dihydro-furan-2-carboxylic acid methyl ester | 247.0 (M + 1) |
| 40 | 5-(3-Ethyl-phenyl)-5-methyl-4-oxo-4,5-dihydro-furan-2-carboxylic acid methyl ester | 259.0 (M − 1) |
| 41 | 5-Cyclohex-1-enyl-5-methyl-4-oxo-4,5-dihydro-furan-2-carboxylic acid methyl ester | 235.0 (M − 1) |
| 42 | 5-(3,5-Dichloro-phenyl)-5-methyl-4-oxo-4,5-dihydro-furan-2-carboxylic acid methyl ester | 301.0 (M + 1) |
| 43 | 5-(3,5-Dichloro-phenyl)-5-methyl-4-oxo-4,5-dihydro-furan-2-carboxylic acid | 285.2 (M − 1) |
| 44 | 5-(3-Iodo-phenyl)-5-methyl-4-oxo-4,5-dihydro-furan-2-carboxylic acid methyl ester | 359.0 (M + 1) |
| 45 | 5-Cyclopentyl-5-methyl-4-oxo-4,5-dihydro-furan-2-carboxylic acid methyl ester | 225.0 (M + 1) |
| 46 | 5-Cyclopentyl-5-methyl-4-oxo-4,5-dihydro-furan-2-carboxylic acid | 209.0 (M − 1) |
| 47 | 5-(3-Cyano-phenyl)-5-methyl-4-oxo-4,5-dihydro-furan-2-carboxylic acid methyl ester | 258.2 (M + 1) |
| 48 | 5-(3-Cyano-phenyl)-5-methyl-4-oxo-4,5-dihydro-furan-2-carboxylic acid | 242.0 (M − 1) |
| 49 | 5-Methyl-4-oxo-5-[((E)-3-propenyl)-phenyl]-4,5-dihydro-furan-2-carboxylic acid | 257.4 (M − 1) |
| 50 | 5-(4-Bromo-5-methyl-thiophen-2-yl)-5-methyl-4-oxo-4,5-dihydro-furan-2-carboxylic acid methyl ester | 331.0 (M + 1) |
| 51 | 5-Biphenyl-3-yl-5-methyl-4-oxo-4,5-dihydro-furan-2-carboxylic acid | 293.0 (M − 1) |
| 52 | 5-[((E)-3-Hex-1-enyl)-phenyl]-5-methyl-4-oxo-4,5-dihydro-furan-2-carboxylic acid | 299.2 (M − 1) |
| 53 | 5-Methyl-5-(4-methyl-thiophen-2-yl)-4-oxo-4,5-dihydro-furan-2-carboxylic acid methyl ester | 251.2 (M − 1) |
| 54 | 5-Methyl-4-oxo-5-(3-vinyl-phenyl)-4,5-dihydro-furan-2-carboxylic acid | 243.0 (M − 1) |

-continued

| Cmpd# | Chemical Name | m/z |
|---|---|---|
| 55 | 5-Methyl-5-(4-methyl-thiophen-2-yl)-4-oxo-4,5-dihydro-furan-2-carboxylic acid | 237.0 (M − 1) |
| 56 | 5-Methyl-5-(5-methyl-thiophen-3-yl)-4-oxo-4,5-dihydro-furan-2-carboxylic acid | 237.0 (M − 1) |
| 57 | 4-Oxo-5-phenyl-5-trifluoromethyl-4,5-dihydro-furan-2-carboxylic acid | 271.2 (M − 1) |

Example 10

Resolution of Compounds of the Invention

Example 10.1

Resolution of 5-(3-Bromo-phenyl)-5-methyl-4-oxo-4,5-dihydro-furan-2-carboxylic acid (Compound 13)

To a solution of racemic 5-(3-Bromo-phenyl)-5-methyl-4-oxo-4,5-dihydro-furan-2-carboxylic acid (4.12 g, 13.87 mmol) in anhydrous $CH_2Cl_2$ (110 mL) was added triethylamine (3.11 g, 30 51 mmol). The solution cooled down to 0° C. and mesyl chloride (1.75 g, 15.26 mmol) was added at the temperature. After 2 h stirring at room temperature, the reaction mixture was again cooled to 0° C. and R(+)-α-methyl-benzyl-amine (1.68 g, 13.87 mmol) was added. After 4 h stirring at room temperature, the reaction mixture was washed with water (100 mL) and brine (70 mL), dried ($MgSO_4$) and concentrated in vacuo. Chromatography on $SiO_2$ (Hexanes/EtOAc, 3/1) gave 1.64 g (30%) of Diastereomer Amide 13A (>98 de % by $^1$H-NMR) and 1.96 g (35%) of Diastereomer Amide 13B (>98 de % by $^1$H-NMR).

Diastereomer Amide 13A: $R_f$=0.5 (Hexanes/EtOAc, 2/1); LC-MS m/z 400 (M+1); $^1$H NMR (400 MHz, $CDCl_3$) δ 7.53 (t, J=1.8 Hz, 1H), 7.46 (ddd, J=8.0, 1.8, 1.0 Hz, 1H), 7.42-7.38 (m, 4H), 7.36-7.31 (m, 2H), 7.23 (t, J=8.0 Hz, 1H), 6.93 (d, J=7.8 Hz, 1H), 6.29 (s, 1H), 5.29 (quint, J=7.1 Hz, 1H), 1.80 (s, 3H), 1.66 (d, J=6.8 Hz, 3H).

Diastereomer Amide 13B: $R_f$=0.6 (Hexanes/EtOAc, 2/1); LC-MS m/z 400 (M+1); $^1$H NMR (400 MHz, $CDCl_3$) δ 7.57 (t, J=1.8 Hz, 1H), 7.49 (ddd, J=8.0, 1.8, 1.0 Hz, 1H), 7.42-7.38 (m, 4H), 7.36-7.31 (m, 2H), 7.26 (t, J=8.0 Hz, 1H), 6.88 (d, J=7.8 Hz, 1H), 6.29 (s, 1H), 5.29 (quint, J=7.1 Hz, 1H), 1.76 (s, 3H), 1.66 (d, J=6.8 Hz, 3H).

(−)-5-(3-Bromo-phenyl)-5-methyl-4-oxo-4,5-dihydro-furan-2-carboxylic acid, [(−)-Compound 13]

A solution of Diastereomer Amide 13B (1.6 g, 4.0 mmol) in dioxane (10 mL) was heated with conc HCl (10 mL) at 107° C. for 29 h (or microwave irradiation at 140° C. for 20 min). After cooling the reaction mixture, it was extracted with ether (50 mL). The separated organic layer was treated with $NaHCO_3$ solution for the acid product to disappear in organic layer. The separated aqueous layer was acidified to pH 2 and extracted with EtOAc (50 mL×2). The combined organic layer was washed with water (50 mL×5) and brine (50 mL), dried ($MgSO_4$), concentrated to give 920 mg (77%) of (−)-Compound 13 as a solid:
$[α]_D$−102.6° (c 1.0, MeOH); LC-MS m/z 297 (M+1); $^1$H NMR (400 MHz, $CDCl_3$) δ 8.45 (brs, 1H), —OH), 7.66 (t, J=1.8 Hz, 1H), 7.49-7.45 (m, 2H), 7.26 (t, J=8.0 Hz, 1H), 6.40 (s, 1H), 1.82 (s, 3H).

(+)-5-(3-Bromo-phenyl)-5-methyl-4-oxo-4,5-dihydro-furan-2-carboxylic acid, [(+)-Compound 13]

Diastereomer Amide 13A was hydrolyzed in a similar manner as described above to give (+)-Compound 13
$[α]_D$+141.0° (c 1.0, MeOH); LC-MS m/z 297 (M+1); $^1$H NMR (400 MHz, $CDCl_3$) δ 8.69 (brs, 1H, —OH), 7.66 (t, J=1.8 Hz, 1H), 7.49-7.45 (m, 2H), 7.26 (t, J=8.0 Hz, 1H), 6.40 (s, 1H), 1.82 (s, 3H).

Example 10.2

Compounds 24, 26 and 56 were separated into their respective (+) and (−) enantiomers using a similar method as described in Example 10.1.

Throughout this application, various publications, patents and published patent applications are cited. The disclosures of these publications, patents and published patent applications referenced in this application are hereby incorporated by reference in their entirety into the present disclosure. Modifications and extension of the disclosed inventions that are within the purview of the skilled artisan are encompassed within the above disclosure and the claims that follow.

Although a variety of expression vectors are available to those in the art, for purposes of utilization for both the endogenous and non-endogenous human GPCRs, it is most preferred that the vector utilized be pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351.

We claim:

1. A compound of Formula (I):

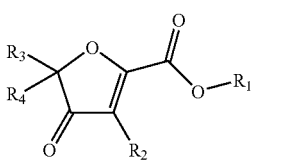

(I)

or a pharmaceutically acceptable salt, hydrate or solvate thereof, wherein:

$R_1$ is H or $C_{1-6}$ alkyl;

$R_2$ is H, halogen, $C_{1-4}$ alkyl or $C_{1-4}$ haloalkyl; and $R_3$ is heteroaryl, which is optionally substituted with 1 to 4 substituents independently selected from the group consisting of $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, aryl, substituted aryl, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heteroaryl, substituted heteroaryl, hydroxyl, nitro and thiol; and $R_4$ is selected from the group consisting of H, $C_{1-6}$ alkyl $C_{3-6}$- cycloalkyl and $C_{1-6}$ haloalkyl wherein each are optionally substituted with 1 to 5 substituents independently selected from the group consisting of $C_{1-6}$ acyloxy, $C_{2-6}$ alkenyl, $C_{1-6}$ alkoxy, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, $C_{1-6}$ alkylamino, amino, carbo-$C_{1-6}$-alkoxy, carboxamide, cyano, $C_{3-7}$ cycloalkyl, $C_{2-6}$ dialkylamino, $C_{2-6}$ dialkylcarboxamide, $C_{2-6}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, nitro and thiol.

2. The compound according to claim 1, or a pharmaceutically acceptable salt, hydrate or solvate thereof, wherein $R_1$ is $C_{1-6}$ alkyl.

3. The compound according to claim 1, or a pharmaceutically acceptable salt, hydrate or solvate thereof, wherein $R_1$ is methyl or ethyl.

4. The compound according to claim 1, or a pharmaceutically acceptable salt, hydrate or solvate thereof, wherein $R_1$ is H.

5. The compound according to claim 1, or a pharmaceutically acceptable salt, hydrate or solvate thereof, wherein $R_2$ is H.

6. The compound according to claim 1, or a pharmaceutically acceptable salt, hydrate or solvate thereof, wherein $R_4$ is methyl.

7. The compound according to claim 1, or a pharmaceutically acceptable salt, hydrate or solvate thereof, wherein $R_4$ is ethyl.

8. The compound according to claim 1, or a pharmaceutically acceptable salt, hydrate or solvate thereof, wherein $R_4$ is $C_{1-6}$ haloalkyl.

9. The compound according to claim 1, or a pharmaceutically acceptable salt, hydrate or solvate thereof, wherein $R_4$ is trifluoromethyl.

10. The compound according to claim 1, or a pharmaceutically acceptable salt, hydrate or solvate thereof, wherein $R_3$ is thienyl optionally substituted with $C_{1-6}$ alkyl, halogen or $C_{1-6}$ haloalkyl.

11. The compound according to claim 1, or a pharmaceutically acceptable salt, hydrate or solvate thereof, wherein $R_3$ is thienyl optionally substituted with methyl, ethyl, F, Cl, Br, I or trifluoromethyl.

12. The compound according to claim 1, or a pharmaceutically acceptable salt, hydrate or solvate thereof, wherein $R_3$ is selected from the group consisting of thiophen-3-yl, thiophen-2-yl, 4-bromo-thiophen-2-yl, 5-methyl-thiophen-2-yl, 5-chloro-thiophen-2-yl, 5-bromo -thiophen-3-yl, 5-chloro-thiophen-3-yl, 4-bromo-5-methyl-thiophen-2-yl, pyridin-3-yl, furan-2-yl, 4-methyl-thiophen-2-yl and 5-methyl-thiophen-3-yl.

13. The compound according to claim 1, or a pharmaceutically acceptable salt, hydrate or solvate thereof, wherein:
   $R_1$ is H;
   $R_2$ is H;
   $R_4$ is methyl, ethyl or trifluoromethyl; and
   $R_3$ is thienyl optionally substituted with $C_{1-6}$ alkyl or halogen.

14. The compound according to claim 1, or a pharmaceutically acceptable salt, hydrate or solvate thereof, wherein:
   $R_1$ is H;
   $R_2$ is H;
   $R_4$ is methyl, ethyl or trifluoromethyl; and
   $R_3$ is selected from the group consisting of thiophen-3-yl, thiophen-2-yl, 4-bromo -thiophen-2-yl, 5-methyl-thiophen-2-yl, 5-chloro-thiophen-2-yl, 5-bromo-thiophen-3-yl, 5-chloro -thiophen-3-yl, 4-bromo-5-methyl-thiophen-2-yl, pyridin-3-yl, furan-2-yl, 4-methyl-thiophen-2-yl and 5-methyl-thiophen-3-yl.

15. The compound according to claim 1 selected from the group consisting of:
   5-Methyl-4-oxo-5-thiophen-3-yl-4,5-dihydro-furan-2-carboxylic acid methyl ester;
   5-Methyl-4-oxo-5-thiophen-2-yl-4,5-dihydro-furan-2-carboxylic acid methyl ester;
   5-(4-Bromo-thiophen-2-yl)-5-methyl-4-oxo-4,5-dihydro-furan-2-carboxylic acid methyl ester;
   5-(4-Bromo-thiophen-2-yl)-5-methyl-4-oxo-4,5-dihydro-furan-2-carboxylic acid;
   5-Methyl-5-(5-methyl-thiophen-2-yl)-4-oxo-4,5-dihydro-furan-2-carboxylic acid methyl ester;
   5-Methyl-5-(5-methyl-thiophen-2-yl)-4-oxo-4,5-dihydro-furan-2-carboxylic acid;
   5-(5-Chloro-thiophen-2-yl)-5-methyl-4-oxo-4,5-dihydro-furan-2-carboxylic acid methyl ester;
   5-(5-Chloro-thiophen-2-yl)-5-methyl-4-oxo-4,5-dihydro-furan-2-carboxylic acid; and
   5-Methyl-4-oxo-5-thiophen-2-yl-4,5-dihydro-furan-2-carboxylic acid; or
   a pharmaceutically acceptable salt, hydrate or solvate thereof.

16. The compound according to claim 1 selected from the group consisting of:
   5-(5-Bromo-thiophen-3-yl)-5-methyl-4-oxo-4,5-dihydro-furan-2-carboxylic acid methyl ester;
   5-(5-Bromo-thiophen-3-yl)-5-methyl-4-oxo-4,5-dihydro-furan-2-carboxylic acid;
   5-(5-Chloro-thiophen-3-yl)-5-methyl-4-oxo-4,5-dihydro-furan-2-carboxylic acid methyl ester;
   5-(5-Chloro-thiophen-3-yl)-5-methyl-4-oxo-4,5-dihydro-furan-2-carboxylic acid;
   5-(4-Bromo-5-methyl-thiophen-2-yl)-5-methyl-4-oxo-4,5-dihydro-furan-2-carboxylic acid;
   5-Methyl-4-oxo-5-thiophen-3-yl-4,5-dihydro-furan-2-carboxylic acid;
   5-Methyl-4-oxo-5-pyridin-3-yl-4,5-dihydro-furan-2-carboxylic acid;
   2-Methyl-3-oxo-2,3-dihydro-[2,2']bifuranyl-5-carboxylic acid;
   5-(4-Bromo-5-methyl-thiophen-2-yl)-5-methyl-4-oxo-4,5-dihydro-furan-2-carboxylic acid methyl ester;
   5-Methyl-5-(4-methyl-thiophen-2-yl)-4-oxo-4,5-dihydro-furan-2-carboxylic acid methyl ester;
   5-Methyl-5-(4-methyl-thiophen-2-yl)-4-oxo-4,5-dihydro-furan-2-carboxylic acid; and
   5-Methyl-5-(5-methyl-thiophen-3-yl)-4-oxo-4,5-dihydro-furan-2-carboxylic acid;
   or a pharmaceutically acceptable salt, hydrate or solvate thereof.

17. The compound according to claim 1, or a pharmaceutically acceptable salt, hydrate or solvate thereof, wherein said compound is essentially the R enantiomer.

18. The compound according to claim 1, or a pharmaceutically acceptable salt, hydrate or solvate thereof, wherein said compound is essentially the S enantiomer.

19. A pharmaceutical composition comprising a compound according to any one of claims 1 and 13 to 18, or a pharmaceutically acceptable salt, hydrate or solvate thereof, in combination with a pharmaceutically acceptable carrier.

20. A pharmaceutical composition according to claim 19 further comprising an agent selected from the group consisting of α-glucosidase inhibitor, aldose reductase inhibitor, biguanide, HMG-CoA reductase inhibitor, squalene synthesis inhibitor, fibrate, LDL catabolism enhancer, angiotensin converting enzyme inhibitor, insulin secretion enhancer and thiazolidinedione.

21. A method of producing a pharmaceutical composition comprising admixing a compound according to claim 1, or a pharmaceutically acceptable salt, hydrate or solvate thereof, and a pharmaceutically acceptable carrier.

22. A compound according to claim 1, or a pharmaceutically acceptable salt, hydrate or solvate thereof, wherein $R_3$ is heteroaryl optionally substituted with 1 to 4 substituents each independently selected from the group consisting of $C_{1-6}$ alkyl, halogen and $C_{1-6}$ haloalkyl.

23. The compound according to claim 1, or a pharmaceutically acceptable salt, hydrate or solvate thereof, wherein $R_4$ is $C_{1-6}$ alkyl.

24. A method of treatment of dyslipidemia comprising administering to an individual in need of such treatment a therapeutically-effective amount of a compound according to claim 1, or a pharmaceutically acceptable salt, hydrate or solvate thereof.

25. A method of treatment of atherosclerosis comprising administering to an individual in need of such treatment a therapeutically-effective amount of a compound according to claim 1, or a pharmaceutically acceptable salt, hydrate or solvate thereof.

26. A method of treatment of coronary heart disease comprising administering to an individual in need of such treatment a therapeutically-effective amount of a compound according to claim 1, or a pharmaceutically acceptable salt, hydrate or solvate thereof.

27. A method of treatment of insulin resistance comprising administering to an individual in need of such treatment a therapeutically-effective amount of a compound according to claim 1, or a pharmaceutically acceptable salt, hydrate or solvate thereof.

28. A method of treatment of obesity comprising administering to an individual in need of such treatment a therapeutically-effective amount of a compound according to claim 1, or a pharmaceutically acceptable salt, hydrate or solvate thereof.

29. A method of treatment of impaired glucose tolerance comprising administering to an individual in need of such treatment a therapeutically-effective amount of a compound according to claim 1, or a pharmaceutically acceptable salt, hydrate or solvate thereof.

30. A method of treatment of hypertension comprising administering to an individual in need of such treatment a therapeutically-effective amount of a compound according to claim 1, or a pharmaceutically acceptable salt, hydrate or solvate thereof.

31. A method of treatment of stroke comprising administering to an individual in need of such treatment a therapeutically-effective amount of a compound according to claim 1, or a pharmaceutically acceptable salt, hydrate or solvate thereof.

32. A method of treatment of Syndrome X comprising administering to an individual in need of such treatment a therapeutically-effective amount of a compound according to claim 1, or a pharmaceutically acceptable salt, hydrate or solvate thereof.

33. A method of treatment of type 2 diabetes comprising administering to an individual in need of such treatment a therapeutically-effective amount of a compound according to claim 1, or a pharmaceutically acceptable salt, hydrate or solvate thereof.

34. A method of raising HDL in an individual comprising administering to said individual a therapeutically-effective amount of a compound according to claim 1, or a pharmaceutically acceptable salt, hydrate or solvate thereof.

* * * * *

UNITED STATES PATENT AND TRADEMARK OFFICE
CERTIFICATE OF CORRECTION

PATENT NO.        : 7,803,837 B2
APPLICATION NO.   : 11/602551
DATED             : September 28, 2010
INVENTOR(S)       : Jae-Kyu Jung, Graeme Semple and Benjamin R. Johnson It is certified that error appears in the above-identified patent and that said Letters Patent is hereby corrected as shown below:

In the Claims:

Col. 76, line 36: In Claim 1, after "alkyl" insert -- , --;

Col. 76, line 40: In Claim 1, after "alkoxy," insert -- $C_{1-6}$ alkyl, --.

Signed and Sealed this
Eighth Day of March, 2011

David J. Kappos
*Director of the United States Patent and Trademark Office*